US009963676B2

(12) United States Patent
Broeckx et al.

(10) Patent No.: US 9,963,676 B2
(45) Date of Patent: May 8, 2018

(54) METHOD FOR ISOLATION AND PURIFICATION OF EPITHELIAL STEM CELLS FROM SKIN

(71) Applicant: Pell Cell Medicals NV, Evergem (BE)

(72) Inventors: Sarah Y. Broeckx, Antwerp (BE); Jan H. Spaas, Bocholt (BE)

(73) Assignee: Pell Cell Medicals NV, Evergem (BE)

( * ) Notice: Subject to any disclaimer, the term of this patent is extended or adjusted under 35 U.S.C. 154(b) by 125 days.

(21) Appl. No.: 14/422,906

(22) PCT Filed: Aug. 20, 2013

(86) PCT No.: PCT/EP2013/067329
§ 371 (c)(1),
(2) Date: Feb. 20, 2015

(87) PCT Pub. No.: WO2014/029778
PCT Pub. Date: Feb. 27, 2014

(65) Prior Publication Data
US 2015/0232807 A1    Aug. 20, 2015

(30) Foreign Application Priority Data

Aug. 23, 2012  (EP) .................................... 12181544

(51) Int. Cl.
*C12N 5/071*    (2010.01)
*A61K 35/36*    (2015.01)

(52) U.S. Cl.
CPC .............. *C12N 5/063* (2013.01); *A61K 35/36* (2013.01); *C12N 2501/11* (2013.01); *C12N 2501/115* (2013.01); *C12N 2509/00* (2013.01)

(58) Field of Classification Search
None
See application file for complete search history.

(56) References Cited

FOREIGN PATENT DOCUMENTS

WO    WO 2005/071063 A1    8/2005

OTHER PUBLICATIONS

Pinto, Isolation and Characterization of Adult Progenitor Cells From Healthy and Laminitic Hoof Tissue, LSU Masters Thesis, May 2012.*
Miki et al., Prostate cell cultures as in vitro models for the study of normal stem cells and cancer stem cells, Prostate Cancer and Prostatic Diseases (2008) 11, 32-39.*
Abramov et al., "Histologic characterization of vaginal vs abdominal surgical wound healing in a rabbit model," *Wound Repair and Regeneration*, vol. 15, pp. 80-86 (2007).
Babaeijandaghi et al., "Accelerated Epidermal Regeneration and Improved Dermal Reconstruction Achieved by Polyethersulfone Nanofibers," *Tissue Engineering: Part A*, vol. 16(11), pp. 3527-3536 (2010).
Beerts et al., "Desmitis of the Accessory Ligament of the Equine Deep Digital Flexor Tendon: A Regenerative Approach," *Journal of Tissue Science & Engineering*, vol. 4(1), pp. 1-7 (2013).
Broeckx et al., "Tenogenesis of Equine Peripheral Blood-Derived Mesenchymal Stem Cells: In vitro Versus In vivo," *Journal of Tissue Science & Engineering*, vol. S11, pp. 1-6 (2012).
Deshiere et al., "Unbalanced expression of CK2 kinase subunits is sufficient to drive epithelial-to-mesenchymal transition by Snail1 induction," *Oncogene*, vol. 32, pp. 1373-1383 (2013).
Roomans, "Tissue engineering and the use of stem/progenitor cells for airway epithelium repair," *European Cells and Materials*, vol. 19, pp. 284-299 (2010).
Singer et al., "Cutaneous Wound Healing," *The New England Journal of Medicine*, vol. 341(10), pp. 738-746 (1999).
Spaas et al., "Stem/Progenitor Cells in Non-Lactating Versus Lactating Equine Mammary Gland," *Stem Cells and Development*, vol. 21(16), pp. 3055-3067 (2012).
Staniszewska et al., "Stem cells and skin regeneration," *Folia Histochemica Et Cytobiologica*, vol. 49(3), pp. 375-380 (2011).
Stingl et al., "Characterization of bipotent mammary epithelial progenitor cells in normal adult human breast tissue," *Breast Cancer Research and Treatment*, vol. 67, pp. 93-109 (2001).
Sundberg, "Skin and Adnexa of the Laboratory Mouse," *Pathophysiology*, Ch. 12, pp. 195-206 (2004).
Wilmink et al., "Differences in second-intention wound healing between horses and ponies: macroscopic aspects," *Equine Veterinary Journal*, vol. 31(1), pp. 53-60 (1999).
Wilmink et al., "Differences in second-intention wound healing between horses and ponies: macroscopic aspects," *Equine Veterinary Journal*, vol. 31(1), pp. 61-67 (1999).
Chen et al., "Therapeutic potential of bone marrow derived mesenchymal stem cells for cutaneous wound healing," *Frontiers in Immunology*, vol. 3, Article 192, pp. 1-9 (Jul. 2012).
Dalal et al., "Role of mesenchymal stem cell therapy in Crohn's disease," *Pediatric Research*, vol. 71(4), pp. 445-451 (Apr. 2012).
Fujimori et al., "Isolation of small-sized human epidermal progenitor/stem cells by Gravity Assisted Cell Sorting (GACS)," *Journal of Dermatological Science*, vol. 56, pp. 181-187 (2009).
Gerseman et al., "From intestinal stem cells to inflammatory bowel diseases," *World Journal of Gastroenterology*, vol. 17(27), pp. 3198-3203 (Jul. 21, 2011).
Grandi et al., "The importance of follicular stem cells in veterinary medicine in the context of skin tumours," *Veterinary Dermatology*, vol. 23, pp. 81-82 (2011).
Lim et al., "Ex vivo expanded SSEA-4+ human limbal stromal cells are multipotent and do not express other embryonic stem cell markers," *Molecular Vision*, vol. 18, pp. 1289-1300 (2012).
Nowak et al., "Isolation and Culture of Epithelial Stem Cells," *Methods Mol Biol.*, vol. 482, pp. 215-232 (2009).

(Continued)

*Primary Examiner* — Suzanne M Noakes
*Assistant Examiner* — Stephen M Chong
(74) *Attorney, Agent, or Firm* — Knobbe, Martens, Olson & Bear, LLP

(57) ABSTRACT

The current invention concerns a method for obtaining a cellular composition comprising epithelial stem cells (EpSCs) from mammalian skin, whereby said composition comprises at least 90% of viable EpSCs, comprising the steps of: —obtaining a mammalian skin sample; —obtaining a cell suspension from said skin sample by performing at least one enzymatic dissociation step; and —culturing said cell suspension under low-attachment conditions. Preferably cellular composition comprises epithelial stem cells derived from the epidermal layer. In a second aspect, the current invention provides for a cellular composition obtained by the method according to the invention.

10 Claims, 18 Drawing Sheets

(56) References Cited

OTHER PUBLICATIONS

Petersen et al., "Interaction with basement membrane serves to rapidly distinguish growth and differentiation pattern of normal and malignant human breast epithelial cells," *Proc Natl Acad Sci USA*, vol. 89, pp. 9064-9068 (Oct. 1992).

Reinshagen et al., "Corneal surface reconstruction using adult mesenchymal stem cells in experimental limbal stem cell deficiency in rabbits," *Acta Ophthalmologica*, vol. 89, pp. 741-748 (2011).

Katwa, "Cardiac myofibroblasts isolated from the site of myocardial infarction express endothelin de novo," *Am J Physiol Heart Circ Physiol*, pp. H1132-H1139 (Jan. 1, 2003).

Li et al., "Enrichment of putative human epidermal stem cells based on cell size and collagen type IV adhesiveness," *Cell Research*, vol. 18(3), pp. 360-371 (Mar. 2008).

Li et al., "Isolation and Culture of Bovine Mammary Epithelial Stem Cells," *Journal of Veterinary Medical Science*, vol. 71(1), pp. 15-19 (Jan. 2009).

Liu et al., "Isolation and Growth of Adult Human Epidermal Keratinocytes in Cell Culture," *J. Invest. Dermatol.*, vol. 71(2), pp. 157-162 (Aug. 1978).

Marcelo et al., "Characterization of a unique technique for culturing primary adult human epithelial progenitor/"stem cells"," *BMC Dermatology*, vol. 12(1), p. 8 (Jun. 24, 2012), in 12 pages.

Rosen et al., "PPARγ is Required for the Differentiation of Adipose Tissue In Vivo and In Vitro," *Molecular Cell*, vol. 4(4), pp. 611-617 (Oct. 1999).

Sharifullina et al., "Comparative Analysis of Different Culture Systems for the Long-Term Cultivation of Human Epidermal Stem Cells," *Tissue Engineering*, Larchmont, New York, US, vol. 12(4), p. 1118 (Oct. 25, 2005).

Spaas et al., "Stem/Progenitor Cells in Non-Lactating Versus Lactating Equine Mammary Gland," *Stem Cells and Development*, vol. 21(16), pp. 3055-3067 (May 11, 2012).

Dontu et al., "In vitro propagation and transcriptional profiling of human mammary stem/progenitor cells," *Genes & Development*, vol. 17, pp. 1253-1270 (2003).

Miki et al., "Identification of Putative Stem Cell Markers, CD133 and CXCR4, in hTERT-Immortalized Primary Nonmalignant and Malignant Tumor-Derived Human Prostate Epithelial Cell Lines and in Prostate Cancer Specimens," *Cancer Res.*, vol. 67(7), pp. 3153-3161 (Apr. 1, 2007).

Reynolds et al., "Clonal and Population Analyses Demonstrate That an EGF-Responsive Mammalian Embryonic CNS Precursor Is a Stem Cell," *Developmental Biology*, vol. 175, Article 0090, pp. 1-13 (1996).

\* cited by examiner

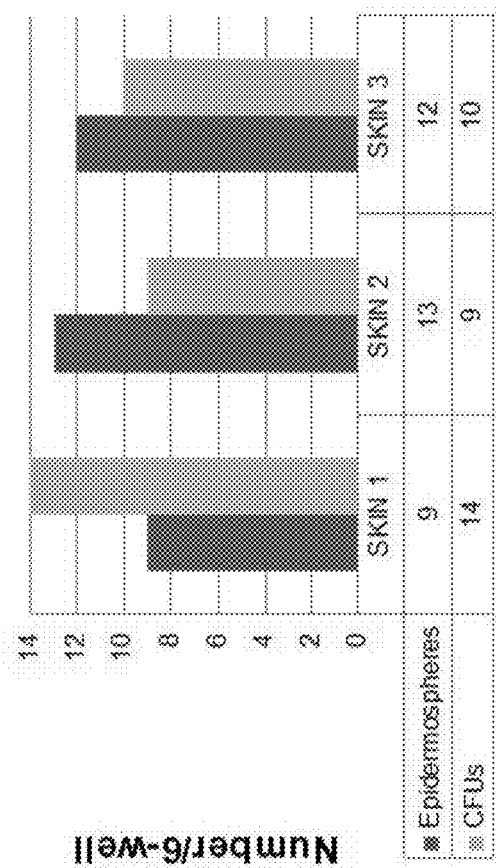
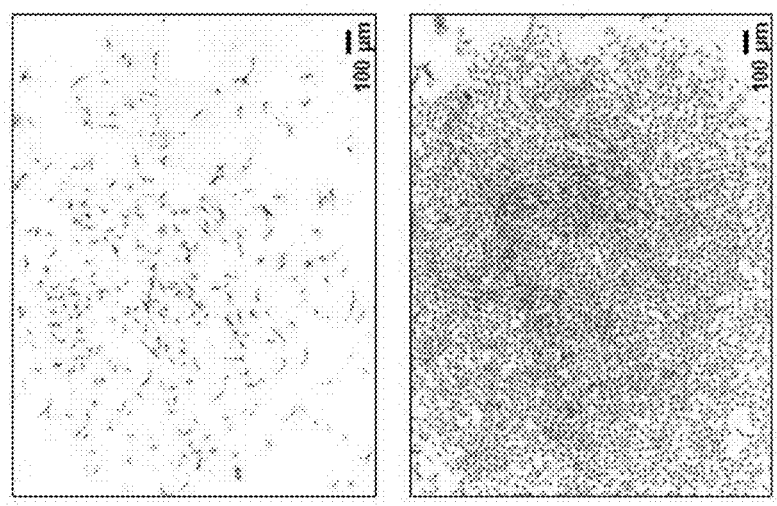
Figure 2

METHOD FOR ISOLATION AND PURIFICATION OF EPITHELIAL STEM CELLS FROM SKIN

CROSS-REFERENCE TO RELATED APPLICATIONS

This application is the U.S. National Phase under 35 U.S.C. § 371 of International Application PCT/EP2013/067329, filed Aug. 20, 2013, which claims priority to EP 12181544.3, filed Aug. 23, 2012.

TECHNICAL FIELD

The invention pertains to the technical field of a method for isolating multipotent stem cells, preferably derived from epithelial samples. The invention also relates to cellular compositions comprising such stem cells, use thereof and differentiated cells derived of these stem cells.

BACKGROUND

Different types of stem cells are being studied because of their capability of forming or regenerating organs and tissues when injuries occur. In contrast to embryonic stem cells, somatic stem cells can be recovered from autologous adult tissues, thereby decreasing the risk of graft rejection. Therefore, the isolation and characterization of stem cells from different tissues, such as bone marrow, adipose tissue, peripheral blood and umbilical cord (blood) are well known. However, the percentage of stem cells is very low in each organ or tissue, and therefore, also the purification is a very important aspect of stem cell research.

Since constant regeneration of the skin is achieved due to somatic stem cell differentiation within the epidermis and the hair follicle, skin may serve as an excellent source of epithelial stem cells (EpSCs) (Grandi et al., 2012; Staniszewska et al., 2011). Hence it has been proposed that EpSCs could be useful in the treatment of several diseases, such as burn wounds, chronic wounds, and ulcers (Draheim and Lyle, 2011). In addition, ectodermal dysplasias, monilethrix, Netherton syndrome, Menkes disease, hereditary epidermolysis bullosa, and alopecias could also benefit from these EpSCs (Draheim and Lyle, 2011).

Therefore, different attempts to sort EpSCs from mammal skin have been described (Fujimori et al., 2009; Nowak and Fuchs, 2009). Fujimori reported the isolation of human epidermal stem/progenitor cells by means of gravity assisted cell sorting. However, sorting cells based on their diameter is quite controversial, since there are a lot of non-stem cells with a small diameter as well. Nowak and Fuchs described fluorescence activated cell sorting (FACS) as a technique to isolate EpSCs from mice. Unfortunately, the cell sorting was performed based on a cell surface marker which is also present on other cell types. In both studies, no thorough characterization was carried out which could have confirmed the origin of the mixed cell populations.

Marcelo et al., 2012 describe a method for producing primary cell cultures from epidermal skin, oral mucosa and ureter by use of a trypsinization step. However, the cells obtained are primary keratinocytes, and hence have lost their multipotency, which makes them less attractive to use.

Recently, the isolation of equine cells with mammary stem/progenitor cell capacities was reported (Spaas et al., 2012) by making use of non-adherent plating conditions. However, the method disclosed herein has several lacunae, resulting in a mixed population of stem cells, their progeny and non-stem progenitor cells, as also previously described by Stingl in 2009. A similar conclusion can be drawn from the method for isolating and culturing bovine mammary epithelial stem cells, as described by Li et al. (2008).

EP 1 414 947 equally described a method for obtaining highly pure populations of stem cell populations based on their property of being able to survive under non-adherent conditions. However, the obtained stem cell population only consisted of dermal stem cells, whereas it was found that no viable stem cells could be purified from the epidermis. Dermal stem cells are however restrictive to the regeneration of dermal cell types (e.g. adipocytes for fat tissue or fibroblasts for connective tissue). Epidermal stem cells are more advantageous when aiming to regenerate epidermal tissue, for instance as treatment for burning wounds or other skin damages (e.g. ulcers).

Researchers are currently also faced with problems identifying EpSCs, and especially from the differentiating EpSCs from MSCs. Although some markers are known (e.g. Spaas et al, 2012; Li et al., 2009; Marcelo et al., 2012; Juxue Li et al., 2008 and Sharifullina et al., 2005), none are found specifically suitable from distinguishing with certainty abovementioned cell populations. As the purity of an isolated cell population is crucial for downstream applications, adequate identification tools are a requisite.

Hence, there remains a need in the art for an improved method for isolation of a pure population of epithelial stem cells, preferably yielding a pure population of stem cells from epidermal origin as well as to provide an adequate marker set to identify the EpSCs. The invention thereto aims to provide an optimized method for isolating, purifying and characterizing EpSCs derived from mammalian skin, which can for instance be used for cosmetic and/or therapeutic purpose.

SUMMARY OF THE INVENTION

The present invention provides a method for obtaining a cellular composition comprising epithelial stem cells (EpSCs) from mammalian skin according to claim 1. In an embodiment of the current invention the method for obtaining a composition comprising at least 90% of viable EpSCs, comprises the steps of:
  obtaining a mammalian skin sample;
  obtaining a cell suspension from said skin sample by performing at least one enzymatic dissociation step; and
  culturing said cell suspension under low-attachment conditions;

Preferably, the cellular composition comprises epithelial stem cells derived from the epidermal layer. The latter allows the specific regeneration of epidermal tissue, for instance as treatment for burning wounds or other skin damages.

The method furthermore preferably includes a selection step, whereby the cells of the cell suspension are selected based on their cell diameter, prior to the culturing of the cell suspension. Preferably the selected cells comprise a diameter between 5 and 150 µm, more preferably between 10 and 100 µm. The latter allows selecting for single cells, which will later on give rise to a pure population of EpSCs. By selecting on diameter, contamination by adult cells is brought to a minimum.

Preferably, the EpSCs are purified from contaminating cells through a selection step under low-attachment conditions, whereby the non-adherent cells forming spherical bodies (epidermospheres) are selected. Said epidermospheres have by preference a radius of between 10 and 1000 µm, more by preference between 25 and 250 µm. Each sphere will preferably contain between 2 and 50 EpScs at 7 days after cultivation.

Characterization of the obtained cellular composition comprising EpSCs occurs preferably by assessing the expression of one molecular marker chosen from the group of CD29, CD44, CD49f, CD90, Ki67, p63 and casein kinase 2β. In another embodiment, the cellular composition comprises EpSCs which are negative for the molecular marker CD105, Pan CK, Wide CK and/or CK18. As such, the nature of the EpSCs can be ascertained, as well as the purity of the yielded cells.

Said cellular composition comprises at least 90% of viable epithelial stem cells. The stem cells are preferably derived from the epidermal layer of mammalian skin.

In a preferred embodiment, the cells are equine derived. The equine system has proven to be an excellent model system for research and therapeutic purposes, as it closely resembles the human system. Hence, in situations where use of specific human EpSCs is not desired or not possible, equine derived EpSCs can provide a suitable alternative.

The current invention also relates to keratinocytes, adipocytes and myofibroblasts which are obtained by the method and/or the cellular composition of the current invention.

In a final aspect, the current invention also relates to the cellular composition or differentiated cells thereof for treatment of tissue and/or organ lesions and or for regeneration of tissue and/or organs.

DESCRIPTION OF FIGURES

FIG. 2 depicts the results of a colony forming unit (CFU) assay with EpSCs purified according to a protocol of the current invention.

FIG. 19 shows the average of the performed experiments.

DETAILED DESCRIPTION OF THE INVENTION

Figure 1:
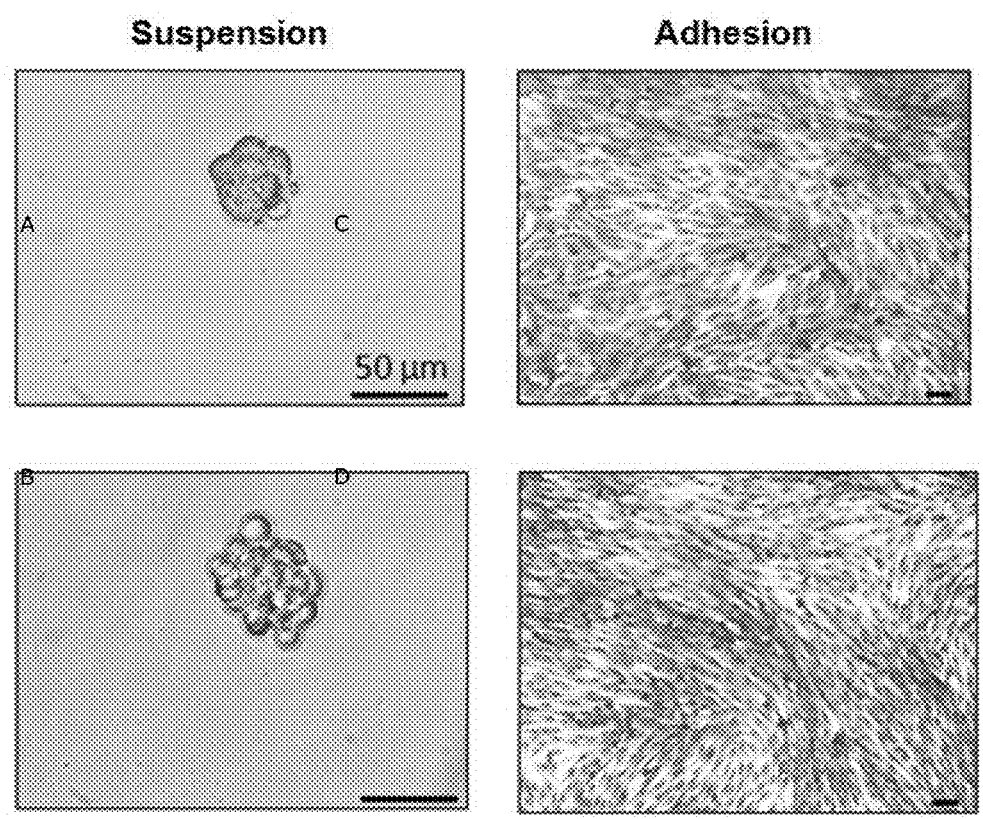
FIG. 1 depicts the purified EpSCs according to the current invention, in a state of suspension (FIGS. 1A and 1B), when plated under ultralow-attachment conditions, and as adherent cells, when plated under normal conditions (FIGS. 1C and 1D).

The present invention concerns a method for obtaining a cellular composition comprising epithelial stem cells (EpSCs) from mammalian skin, whereby said composition comprises at least 90% of viable EpSCs. Due to their proliferative and differentiating nature, these compositions can be used for various applications, such as treatment of burn wounds, breast reconstruction or tissue generation.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In a first aspect, the invention provides for a method for obtaining a cellular composition comprising epithelial stem cells (EpSCs) from mammalian skin, whereby said composition comprises at least 90% of viable EpSCs.

In one of the embodiments, said method comprises the steps of:
- obtaining a mammalian skin sample;
- obtaining a cell suspension from said skin sample by performing at least one enzymatic dissociation step on said skin sample; and
- culturing said cell suspension under low-attachment conditions.

Preferably, the epithelial stem cells are derived from the epidermal layer. Therefore, depending on the nature of the skin sample, the method preferably includes a separation step, whereby the dermis is at least partially separated from the epidermis. This separation can occur mechanically only, by use of for instance forceps, scalpel or tweezers or by use of dissociation agents such as enzymes. In one embodiment, both methods can be combined.

As used herein, the term "epithelia" and "epithelium" is meant the cellular covering of internal and external body surfaces (cutaneous, mucous and serous), including the glands and other structures derived therefrom, e.g., corneal, esophageal, epidermal, and hair follicle epithelial cells. Other exemplary epithelial tissue includes: olfactory epithelium, which is the pseudo-stratified epithelium lining the olfactory region of the nasal cavity, and containing the receptors for the sense of smell; lung epithelium, which lines the inside of the lungs and the alveoli; glandular epithelium, which refers to epithelium composed of secreting cells; squamous epithelium, which refers to epithelium composed of flattened plate-like cells. The term epithelium can also refer to transitional epithelium which is characteristically found lining hollow organs that are subject to great mechanical change due to contraction and distention, e.g. tissue which represents a transition between stratified squamous and columnar epithelium. The term "epithelialization" refers to healing by the growth of epithelial tissue over a denuded surface.

By "skin" is meant the outer protective covering of the body, consisting of the epidermis, the basement membrane and the dermis, and is understood to include sweat and sebaceous glands, as well as hair follicle structures. Throughout the present application, the adjective "cutaneous" may be used, and should be understood to refer generally to attributes of the skin, as appropriate to the context in which they are used.

By "skin sample" is meant a sample or biopsy of the skin, said sample comprising epidermis (comprising stratum corneum, stratum lucidum, stratum granulosum, stratum spinosum and stratum basale), the basement membrane and dermis.

By "epidermis" is meant the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, conified non-nucleated cells. In the epidermis of the general body surface, the clear layer is usually absent. An "epidermoid" is a cell or tissue resembling the epidermis, but may also be used to refer to any tumor occurring in a noncutaneous site and formed by inclusion of epidermal elements.

By "dermis" is meant the innermost layer of the skin in vertebrate animals. The dermis lies under the epidermis and contains nerve endings and blood and lymph vessels. In mammals, the dermis also contains hair follicles and sweat glands.

By "differentiation" is meant the formation of cells expressing markers known to be associated with cells that are more specialized and closer to becoming terminally differentiated cells incapable of further division or differentiation.

By "lineage committed cell" is meant a progenitor cell that is no longer pluripotent but has been induced to differentiate into a specific cell type.

By "proliferation" is meant an increase in cell number.

By "non-adherent clusters" is meant that the cells of the invention are able to adhere to each other and form clusters which increase in size as the cells proliferate, but these cells do not adhere to the substratum and grow in suspension, wherein the substratum is uncoated tissue culture plastic or a culture vessel coated with a neutral coating such as agar or gelatin.

By "dissociating a sample" is meant to separate tissue into single cells, smaller cell clusters, or smaller pieces of tissue.

Figure 11:
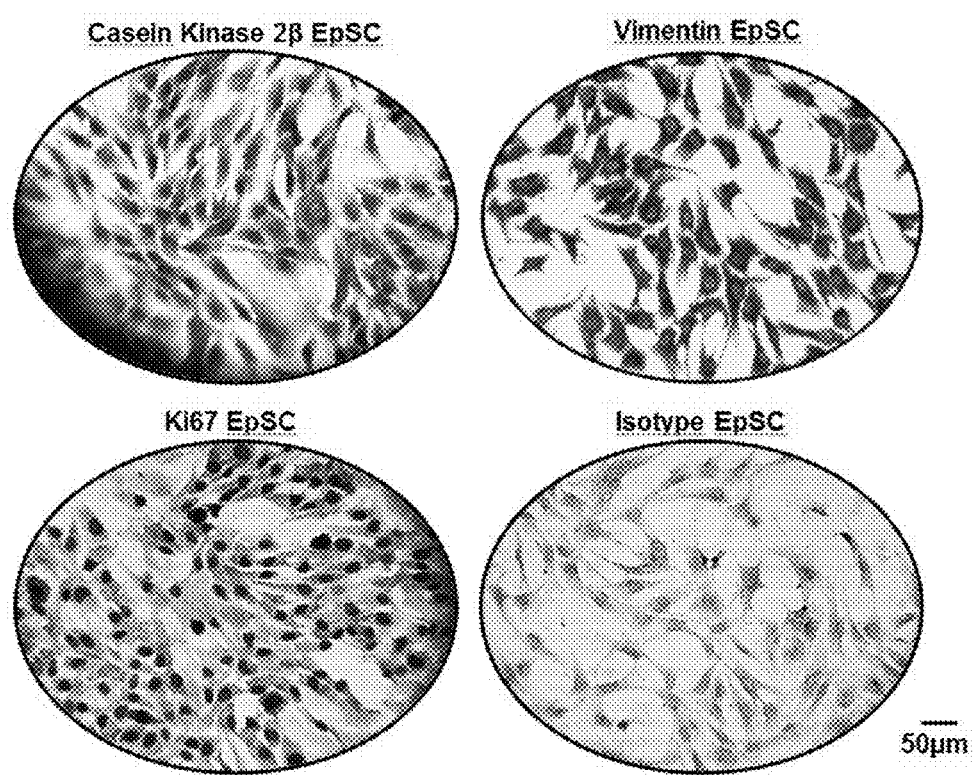
FIG. 11 depicts the presence of Casein Kinase 2β, vimentin and Ki67 on epithelial EpSCs isolated from a human sample according to an embodiment of the current invention.
Figure 12:
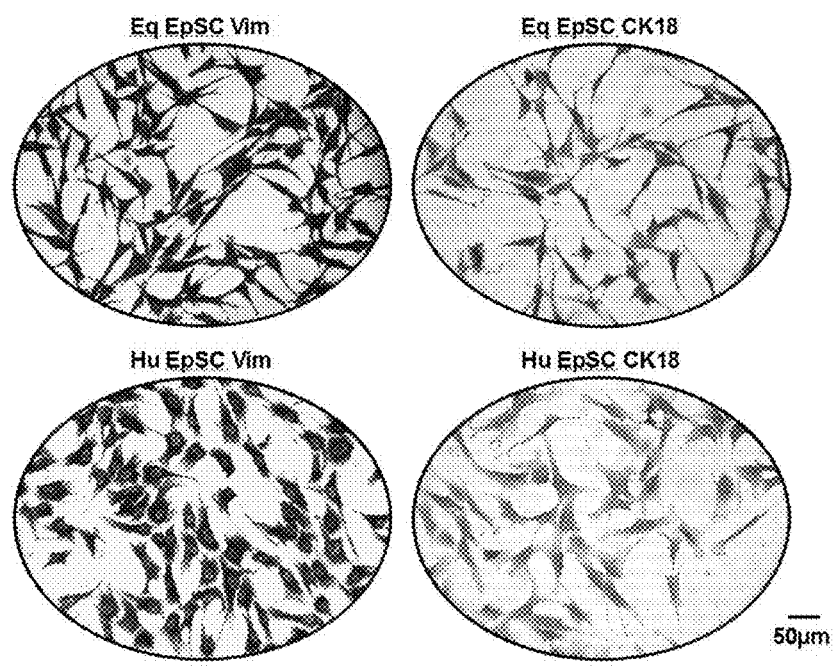
FIG. 12 shows the presence of vimentin and the absence of cytokeratin 18 (CK 18) in equine and human derived EpSCs isolated according to the current invention.
Figure 13:
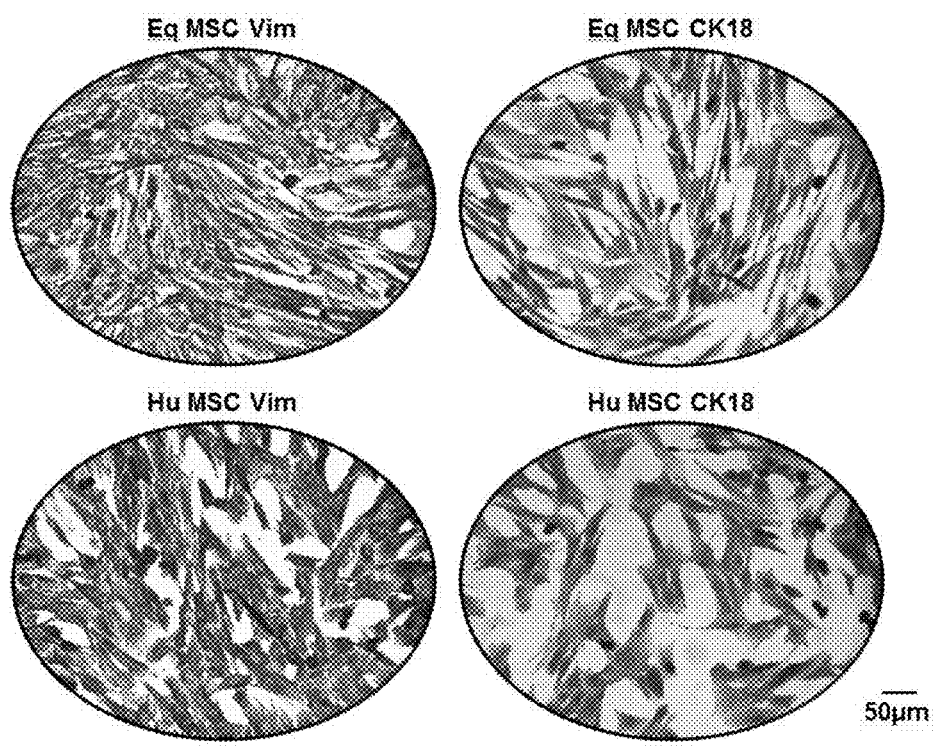
FIG. 13 shows the presence of both vimentin and cytokeratin 18 (CK18) in equine and human derived mesenchymal stem cells.

Ideally, the epidermis will be completely separated from the dermis. In practice, this is rather difficult to perform, as a certain degree of contamination with dermal stem cells is difficult to be avoided. In one embodiment of the current invention, the ratio between epidermal, epithelial stem cells and dermal stem cells in the obtained cellular composition will preferably be between 80:20 and 100:00, more preferably between 90:10 and 100:0. Most preferably the total presence of the epidermal stem cells in the cellular composition will be more than 95%. Presence or absence of dermal cells in the obtained cellular composition can be discerned by use of appropriate markers such as for instance, but not limiting to cytokeratin (negative for epidermal stem cells, positive for dermal stem cells), casein kinase subunit 2β (Deshiere et al., 2012), p63 and CD105. Flow cytometry results with CD105 marker on a cellular composition obtained through the current invention show a percentage of CD105 positive cells of 5%±3% (results not shown). This corresponds with the background signal as negative cells showed a similar result. FIGS. 11-12 show the presence of casein kinase subunit 2β (FIG. 11) as well as vimentin (FIG. 12) in EpSCs derived from a human, epidermal sample. Human and equine derived EpSCs were negative for cytokeratin 18 (CK18) (FIG. 12). Mesenchymal stem cells were shown to be positive for both cytokeratin 18 and vimentin (FIG. 13). Moreover, equine EpSCs were positive for p63 (FIG. 18), whereas it has been reported that MSCs are negative for p63 (Lim et al., 2012; Reinshagen et al., 2011).

The results proof the distinct nature of the EpSCs purified according to the current invention, and shows that they are predominantly derived from the epidermal layer.

The term 'enzymatic dissociation step' is to be understood as any step, involving an enzyme or a solution comprising an enzyme, which results in complete or partial disconnection of cells normally present within a geometrically arranged two-dimensional or three-dimensional structure, e.g. a tissue sample. As a final result, a cell solution is eventually obtained, preferably mainly consisting of single cells and/or cell clusters. Dissociation occurs preferably by breaking of the intercellular adhesion bonds of cells.

In one embodiment of the current invention, said enzymatic dissociation step involves a trypsinization step. Said trypsinization step should be performed under conditions which allow a release of the dermo-epidermal junctions followed with detachment of the epidermis from the dermis. Trypsinization can be performed at room temperature (20-25° C.) or at lower or higher temperature (e.g. 37 or 38° C.), for a time period sufficiently long to destroy cell-cell connections.

By preference, said enzymatic dissociation step is followed by a mechanical separation of the epidermal from the dermal layer. After said mechanical separation of epidermal of dermal layer, a cell suspension can be obtained, preferably by means of one or more enzymatic dissociation steps.

In a more preferred embodiment, said enzymatic dissociation step will increase the isolation percentage of the stem cells. Suitable enzymatic solutions that can be used for this second enzymatic dissociation step may comprise Collagenase type I, Collagenase type II, Collagenase type III, papain and Dispase. Preferably, said second enzymatic dissociation step comprises Collagenase type III.

In a further embodiment, a selection step is incorporated which enables selecting and isolating that pool of cells which will eventually give rise to the cellular composition of epithelial stem cells. Preferably, said selection present in the cell suspension is based on cell diameter. The selection step occurs prior to the culturing of cell suspension. In a preferred embodiment, the cell diameter of the selected cells will be between 5 and 150 µm, more preferably between 10 and 100 µm. In one embodiment, selection occurs through filtration of the cell solution with a filter having a suitable pore size for selection of cells within the desired cell diameter range. In another embodiment, selection may be performed through cells sorting means, such as a cell sorter or flow cytometer. In general, the presence of cell clusters should be avoided, in order to eliminate the risk of contamination with adult cells. Cell clusters of adult cells are capable of surviving the low adherent conditions during purification.

The method of the current invention equally includes a culturing step of the cell solution under low-adherent circumstances. Such "low-adherent circumstances" should be understood as those conditions which allow culturing cells in suspension, preferably for propagation of said cells, whereby adherence of the cells to a substrate is reduced to a minimum. More specifically, it refers to the use of specially designed tissue culture equipment, such as plates or flasks, which prevent the hydrophobic and ionic interactions of cells with a substrate. Such conditions can for instance be obtained by providing the tissue culture equipment with a hydrogel layer which is hydrophilic and neutrally charged. Hence, when cultured under these conditions, cells will be kept in suspension. Ultra-low attachment plates are readily known and commercially available. Stem cells, much more than other cells, have the capability to survive and proliferate under these ultralow-attachment conditions. Soon after culturing, the stem cells will start forming spherical cell clusters in the cell medium, so called epidermospheres (cfr. embryoid bodies of embryonic stem cells). Said epidermospheres have by preference a radius of between 10 and 1000 µm. By preference, said epidermospheres contain 2 to 50 EpSCs at 7 days of cultivation.

Preferably, the cells will be plated in a medium (EpSC medium), specifically optimized for culturing and proliferating of EpSCs. In an embodiment of the current invention, this cell medium will comprise growth factors, chosen from the group comprising FGF, bFGF and/or EGF. Enrichment and selection of the resulting non-adherent cells occurs by harvesting of the EpSC medium comprising the epidermospheres, centrifugation and removal of supernatant (along with dead cells and debris), re-suspension of the cells in EpSC medium and subsequent plating on ultralow-attachment plates. By repeating this purification round, eventually a highly pure population of EpSCs will be obtained. Depending on the desired level of purity of the EpSCs, several multiplication rounds may be desired. In a preferred embodiment, culturing under ultralow-adherence conditions occurs for minimal 7 days.

In general, the obtained population of non-adherent cells comprises at least 90% epithelial stem cells. More preferably, the obtained cell population will comprise at least 95% epithelial stem cells, even more preferably at least 99%. In a most preferred embodiment, the obtained cell population will consist out of 100% pure epithelial stem cells.

If desirable (e.g. when the yield of stem cells is low), multiplication of the obtained cellular composition of EpSCs may occur by plating the cells under adherent conditions. The latter allows for multiplication of the cells.

Figure 9:
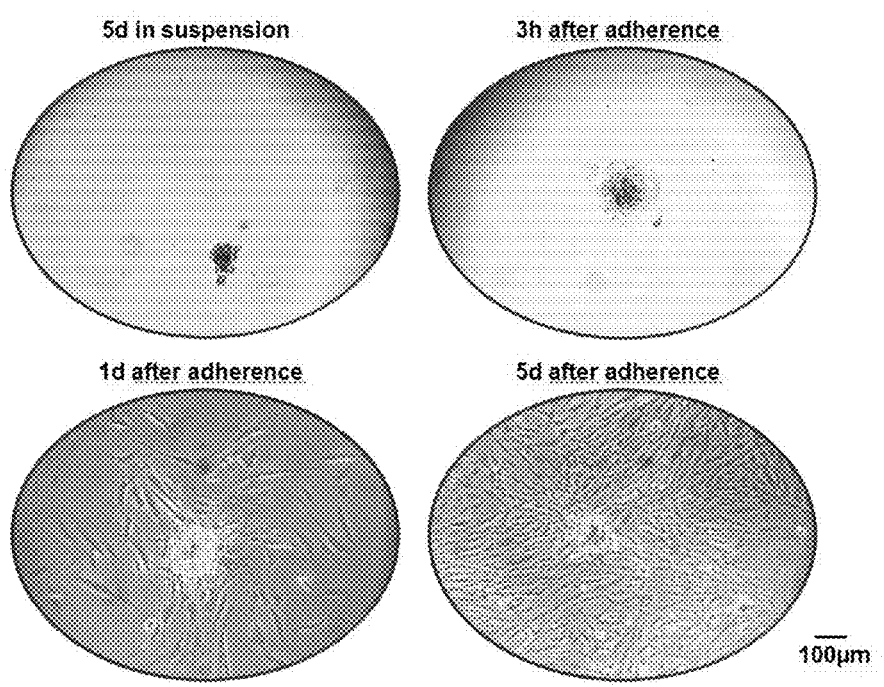
FIG. 9 depicts the spreading of the epidermospheres according to an embodiment of the current invention, after transferring from a cell plate under low-attachment conditions (first well) to a normal culture plate (subsequent wells) which allows adherence of the cells. Cells show a remarkable proliferation speed when plated under conditions that allow attachment to a substrate.

FIG. 9 shows the remarkable spreading and proliferation plate of epidermospheres when transferred to a low-attachment plate to a plate allowing adherence of the cells. Cell spreading and proliferation can be discerned after no little than 3 hours.

In order to ascertain that indeed a pure cellular composition of EpSCs has been obtained, the obtained cellular composition will be tested by use of suitable markers. In an embodiment of the current invention, the cellular composition comprises EpSCs which express at least one molecular marker chosen from the group of CD29, CD44, CD49f, CD90, Ki67, p63 and casein kinase 2β. Moreover, in a further embodiment, the cellular composition comprises EpSCs which are negative for molecular marker CD105, Pan CK, Wide CK and/or CK18.

Figure 19:
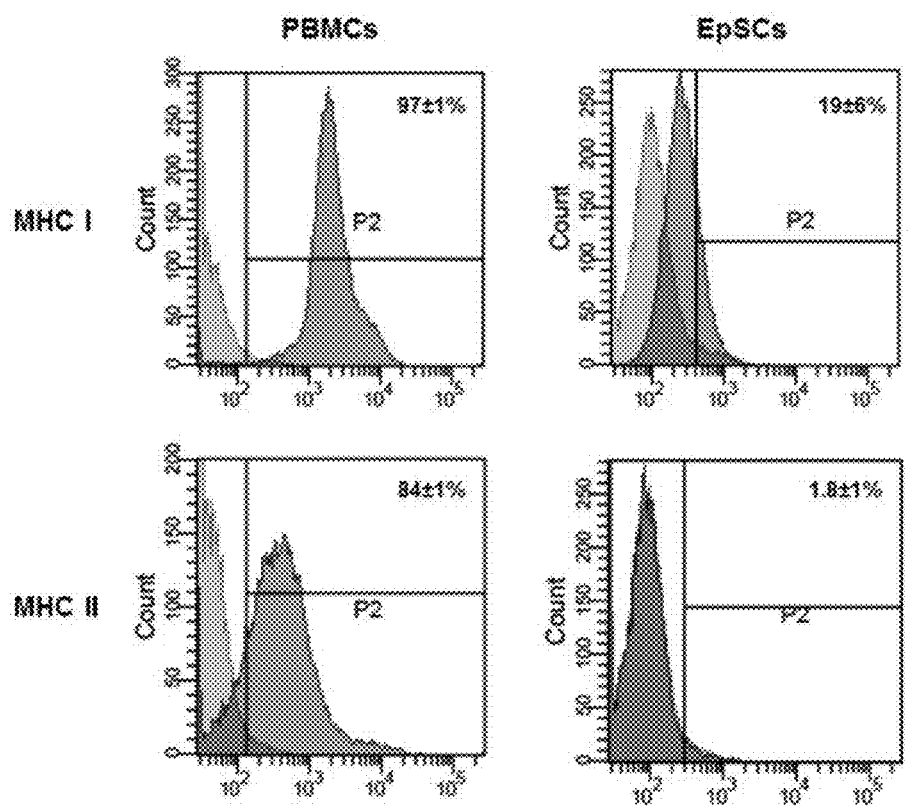
FIG. 19 shows expression (albeit low) of MHCI and absence of MHCII expression on EpSCs. Expression was analysed by means of flow cytometry. Experiments were performed in threefold and with peripheral blood mononuclear cells (PBMCs) as positive control.

By preference, said EpSCs are furthermore slightly positive for MHCI and negative for MHCII (see FIG. 19).

In a most preferred embodiment, a combination of markers, both positive and negative is tested in order to come to a conclusive result. The latter allows distinguishing the nature of the isolated and purified EpSCs, and establishing the purity of the obtained sample. Cells which do not comply with the presence and/or absence of above-mentioned markers should not be considered as EpSCs (but may for instance be MSCs or adult cells). By the method according to the current invention, a very high yield of pure EpSC population may be obtained (up to 100%). The latter is of crucial importance to any downstream application.

In further embodiment, the EpSCs of the cellular composition are capable of differentiating towards keratinocytes, myofibroblast and adipocytes.

The method according to the current invention can be performed on all types and origins of epidermal tissue. Preferably mammalian skin will be the basis of the obtained cellular composition. Said mammalian skin can be obtained for instance from, but not limiting to humans, mice, dogs, cats, sheep, cows, pigs, horses, rabbits, rats, guinea pigs, other rodents, etc.

In one of the preferred embodiments, EpSCs are isolated and purified from a human subject. In another preferred embodiment, the isolation occurs from equine derived samples. Various reasons favor using equine skin samples for the isolation and purification protocol, with or without extrapolation of the protocol to other animal species afterwards. First of all, skin of horses has a high resemblance with human skin, much more than other animals. In contrast to horses and humans, mice don't possess apocrine sweat glands (Sundberg, 2004), cows have a rather thick dermal layer and dogs have a more developed subcutis. It was moreover found by the inventors that all protocols developed for either human or equine isolation and purification of EpSCs could be readily extrapolated to the other species (human to equine and vice versa). Secondly, equine skin samples are easy to obtain through slaughterhouse collection. Thirdly, in horses as well as humans second intention wound healing consists of 4 comparable phases (inflammatory-granulation-contraction-epithelialization) (Singer and Clarck, 1999; Wilmink et al., 1999a&b). Lastly, as for use of the equine derived EpSCs is concerned: extended wounds of the distal limbs are one of the most common dermatological pathologies in horses and tend to have a long recovery period and poor response to conventional therapies (Wilmink et al., 1999a). For all these reasons, the horse was considered as one of the ideal models for epithelial stem cell research and possible clinical trials afterwards in general, and for isolating EpSCs according to the current invention.

The obtained sample may be derived from various body parts, e.g. limbs, the trunk, the foreskin, the head, lung and intestinal epithelium, olfactory epithelium etc.

In a further aspect, the cellular composition or differentiated cells thereof may serve as a treatment of tissue and/or organ lesions and/or for regeneration of tissue and/or organs. By preference, said tissue or organ is from ectodermal, mesodermal or from ectomesodermal origin. Examples of possible tissue or organs are, but not limiting to skin tissue, mammary tissue, mammary gland, nerves, bone tissue, cartilage tissue, muscle tissue, tendon or ligament tissue. The cellular composition or differentiated cells thereof obtained by the current invention will allow for instance regenerative medicine and cosmetic interventions, e.g. for tissue regeneration and/or hair regeneration. Other purposes might include the revitalization of scar tissue or treatment of burning wounds. In a further aspect, the cellular composition or differentiated cells thereof according to the current invention can be used in the treatment of a vast amount of illnesses. Dysfunction of the airway epithelium for instance can lead to different pulmonary pathologies, stem cells have been suggested as a possible treatment for bacterial bronchopneumonia, cystic fibrosis, acute respiratory distress syndrome, chronic obstructive lung disease and pulmonary fibrosis, pulmonary hypertension and pulmonary edema (Roomans, 2010). Since in the past epithelial stem cells were too difficult to obtain and to identify, researchers preferred treating these diseases with mesenchymal stem cells, because they are well-known and extensively characterized. Also intestinal (epithelial) stem cells have been put at the origin of intestinal pathologies, such as Crohn's disease and ulcerative colitis (Gersemann et al., 2011), but until present only treatments with mesenchymal stem cells have been reported for these illnesses (Dalal et al., 2012). In addition, the use of mesenchymal stem cells has even been described for epidermis repair during wound healing in mice (Chen et al., 2012). However, in order to fully regenerate all kinds of epithelial tissues, the isolation, purification and afterwards the clinical applications of epithelial stem cells are indispensable.

Other application fields of the current invention involve treatment of ectodermal dysplasias, monilethrix, Netherton syndrome, Menkes disease, hereditary epidermolysis bullosa, and alopecias. In addition, breast enlargements or reconstitutions could be treated by the cell composition described in the current invention. Other possible therapeutic application involves treatment of cartilage and muscle disorders (mesodermal lines).

Hence, the cellular composition according to the current invention or differentiated cells thereof may be used for the manufacturing of a medicament against above-mentioned diseases and conditions. The composition of EpSCs can be differentiated into lineage committed cells such as keratinocytes, myocytes, melanocytes or adipocytes, depending on the addition of specific cell medium supplemented with suitable growth factors and differentiating agents.

In one embodiment, said EpSCs of the cellular composition are capable of differentiating towards keratinocytes, myofibroblast, melanocytes and adipocytes. Hence, the current invention equally relates to keratinocytes, melanocytes, adipocytes and/or myofibroblasts derived from a cellular composition according to current invention, whereby the cellular composition is preferably obtainable according to the method of the current invention.

Figure 6:
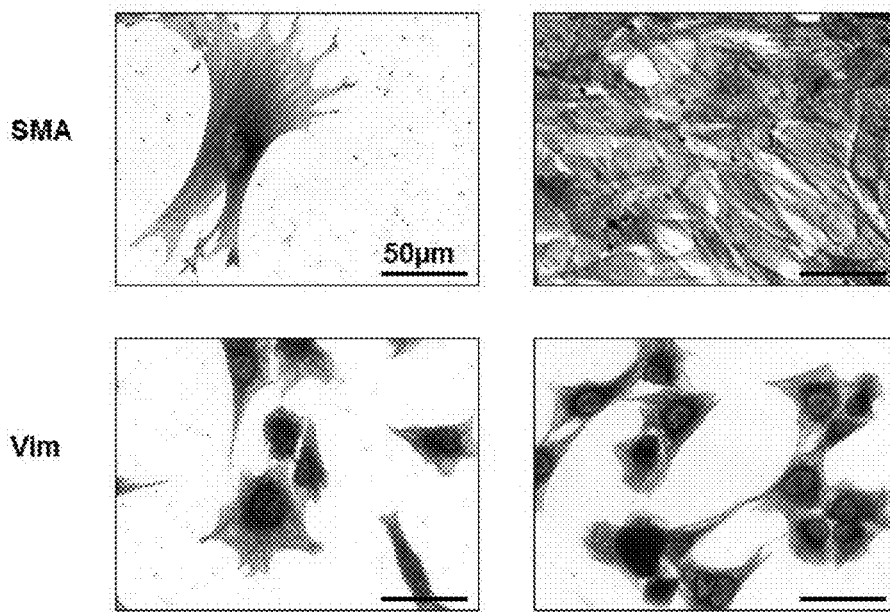
Figure 17:
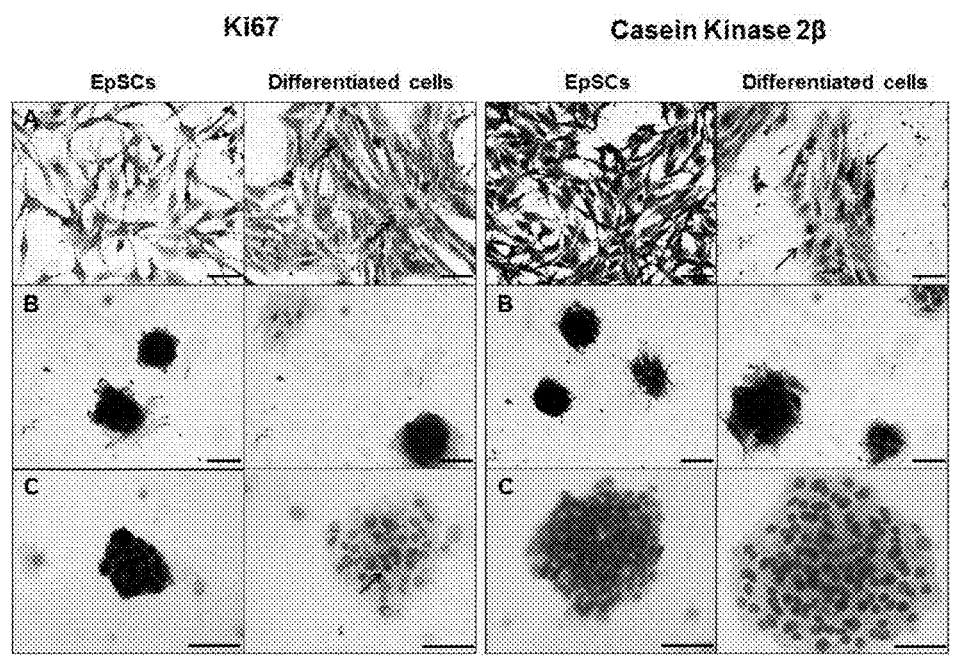
FIG. 17 shows Ki67 and Casein Kinase 2β expression on undifferentiated EpSCs according to the current invention in adhesive cultures (A), epidermospheres after 1 hour of adherence (B) and epidermospheres on cytospins (C). Bars represent 50 µm.

Said keratinocytes may be characterized in that they express CK18, Pan CK, Wide CK and p63. By preference, said keratinocytes exhibit a cobblestone morphology. Moreover, the presence of marker CK2β (normally present in EpSCs) sharply decreases upon differentiation (FIG. 17). Said adipocytes may be characterized in that they exhibit a round or rounded morphology with the presence of lipid droplets in the cells (visualized by Oil Red O staining, FIG. 7). Said myofibroblasts according to the current invention they are positive for molecular markers vimentin and smooth muscle actin (FIG. 6). By preference, they exhibit a tubular or tubular-like morphology.

This proofs the multipotent nature of the obtained stem cells. As such, the cellular composition according to the current invention allows for the regeneration of a wide range of cell types which can be used in a vast amount of applications.

The invention is further described by the following non-limiting examples which further illustrate the invention, and are not intended to, nor should they be interpreted to, limit the scope of the invention.

EXAMPLES

Example 1

Isolation and purification of skin epithelial stem cells, e.g. isolated from the neck
Isolation Protocol
Take at least 1 cm² of mammalian skin, after clipping and surgical preparation (scrubbing with iodide and disinfecting with 70% ethanol) of the sampling site.
  Treat tissue sample with 0.25% trypsin-EDTA solution at a temperature equal to or lower than room temperature, for minimal 1 hour or until cells have obtained the desired range of dissociation (single cell suspension, release dermo-epidermal junctions).
Peel the skin (remove the epidermis from the dermis) and remove hair if present
Cut the epidermis into small pieces
Optionally: second enzymatic dissociation step with 0.2%-2% collagenase III (168.000 Units/g). This will increase the isolation percentage.
Inactivate the collagenase III by adding cell medium (e.g. EpSC medium: DMEM/F12, 20% FBS, 2% P/S/F, 10-20 ng/ml hr-bFGF, 10-20 ng/ml EGF) Filter the suspension through filter with a range in diameter of ≥10 µm and ≤100 µm. Selection based on the diameter improves the pureness of the cell suspension.
Wash cells with EpSC medium. Repeat several times if desired.
Purification Protocol
Filter cell solution with a filter ranging in diameter of 10 µm and 100 µm.
Count and plate the cells (approximately $10^6$ cells) directly on a well of an ultralow-attachment plate in EpSC medium for purification of the EpSCs (Well A) (FIG. 1, suspension).
At day 2:
  ⇨ Refresh the EpSC medium by centrifugation at 350 G for 7 minutes and remove the supernatant.
  ⇨ Resuspend the cells and plate on ultralow-attachment plate
  ⇨ Repeat at least one time
  ⇨ If there are not enough EpSCs after purification, plant all the EpSCs directly to a tissue culture plate for multiplication of the EpSCs before further experiments can be done (FIG. 1, adhesion). Otherwise, dissociate the epidermospheres by using 0.25% trypsin-EDTA and subsequently filter them through a sterile filter with a range in diameter of ≥10 µm and ≤100 µm for further experiments.

Figure 3:
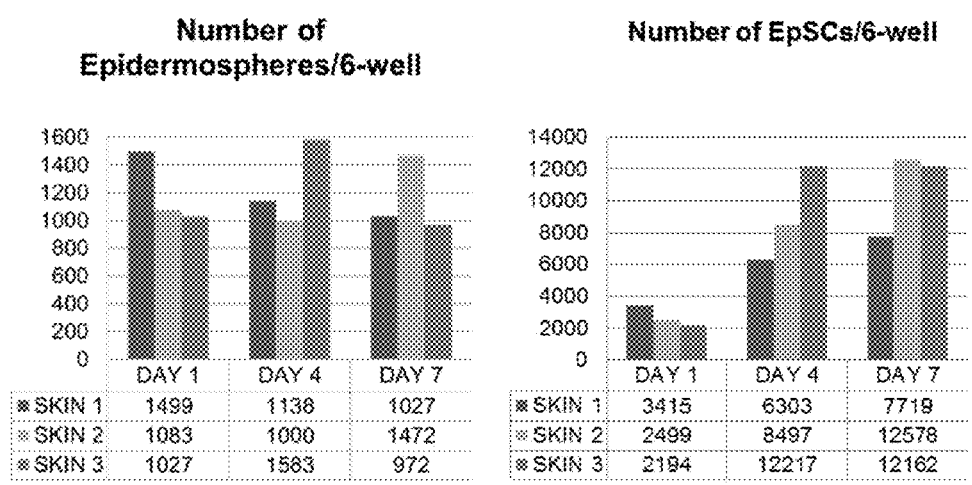
FIG. 3 depicts the results of an amplification assay with EpSCs purified according to a protocol of the current invention.

Characterization of Skin-Derived EpSC
1) Reagents Needed for Differentiation
Keratinocyte differentiation medium:
  DMEM/F12
  20% FBS
  2% P/S/F
  5 µg/ml insulin
  1 µg/ml hydrocortisone 0.1 mM beta-mercaptoethanol
Adipogenic inducing medium:
  DMEM
  15% rabbit serum
  2% P/S/F
  10 µM dexamethasone
  0.5 mM 3-isobutyl-1-methyl-xanthine 10 µg/ml recombinant human (rh)-insulin
  0.5 mM indomethacin
2) Create Single Cell Suspension
Bring the epidermospheres of the ultralow-attachment plate into a 15 ml tube. The following tests may be performed with or without amplification on an adherent culture vessel first in order to increase the cell number if there would be a shortage of EpSCs. FIG. 9 depicts the remarkable proliferation rate of EpSCs when cultured under normal conditions which allow substrate attachment. Merely after 3 hours of culturing, spreading of the cells is observable.
If there are enough epidermospheres:
  Trypsinize EpSCs with 0.25% Trypsin-EDTA for 10 minutes at 37° C.
  Poor the cells through a sterile filter with a range in diameter of ≥10 µm and ≤100 µm for further experiments.
  Count the cells for further use
2a) CFU Assay
Plant 10 EpSCs/6-well on 3 wells of an adherent culture vessel and 10 EpSCs/6-well on 3 wells of a Corning ultralow-attachment plate (ULA Plate).
  For adhered CFU: fix and stain with Cristal Violet if visualization is wanted.
  For both adhered and spherical CFUs: count CFU's.
  Frequency of CFU's=#CFU's/#planted cells×100.
When seeding a small number of cells (10-100, but in this case 10) on a relatively large surface, after approximately 1 week (6-9 days) it is possible to count the total number of colony forming units (CFUs) that were formed. Since it is hypothesized that each stem cell can form one CFU, the total number of CFUs represents the self-renewal rate of the EpSCs and the number of stem cells that are present. For planting 10 EpSCs it was found that approximately 10 CFUs were formed in adhesion (FIG. 2: the beginning of a CFU left above, and the final stage left bottom) as well as in suspension. These tests were performed in three mammals, each in triplicate. Bars present 100 µm.
2b) Amplification Assay
Plant 1000 cells/6-well on 3 wells of a Corning ultralow-attachment plate (ULA Plate). Evaluate (epidermosphere count/well and EpSC count/epidermosphere) at day 1, 4 and 7.
We propose a method for enhancing the proliferation of the epidermosphere-derived EpSCs on a non-coated culture vessel. After planting 1000 EpSCs, at the first day, a large number of epidermospheres were already noticed and each sphere contained several EpSCs (FIG. 3). Although, the average number of spheres remained the same over the one week cultivation period, the number of EpSCs varied considerably (FIG. 3). When seeding the epidermospheres on cell culture coated surfaces, the spheres attached and seemed to multiply in a faster way than in suspension (FIG. 9).

2c) Differentiation

Differentiation towards adult epithelial cells and myocytes

Plant 5000 cells per 4- or 24-well culture plate (this can also be done on smaller or larger culture vessels, as long as the initial concentration remains the same).

A) EPITHELIAL CONTROL
    Culture for 10 days and refresh twice a week with the EpSC medium in the 4- or 24-well plate.
B) KERATINOCYTE DIFFERENTIATION
    Culture for 10 days and refresh twice a week with keratinocyte differentiation medium in the 4- or 24-well plate.
Immunocytochemistry
    ⇨ PanCK (mouse, 1:50)
    ⇨ Wide CK (rabbit, 1:50)
    ⇨ CK18 (mouse, 1:30)
    ⇨ SMA (mouse, 1:200)
    ⇨ Vimentin (mouse, 1:100)
    ⇨ Casein kinase 2β(rabbit, 1:50)
    ⇨ p63 (rabbit, 1:200)
    ⇨ Isotype PRRSV (mouse, 1:50)
    ⇨ Isotype HSA (rabbit, 1:200)

Figure 8:
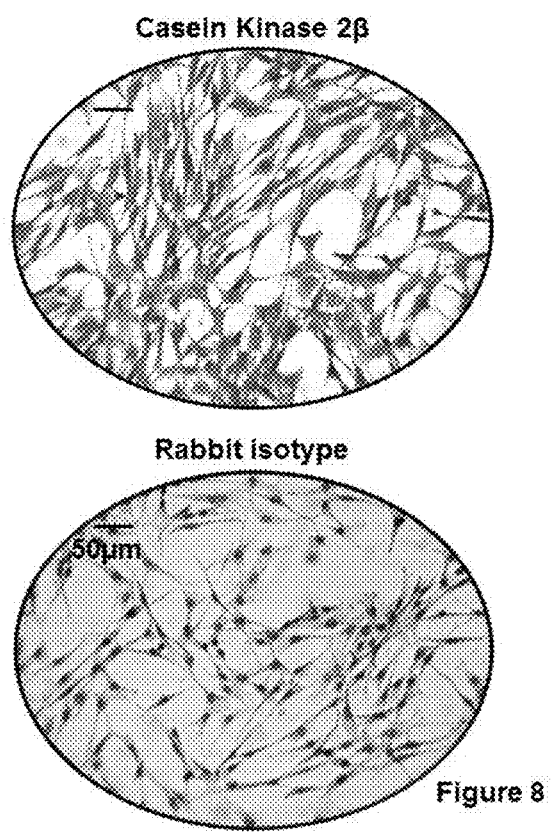
FIG. 8 shows that immunocytochemistry with a casein kinase 2β on the obtained cell composition confirms the epithelial nature of the stem cells.

Immunocytochemistry performed on the undifferentiated EpSCs showed a confluent monolayer of spindle shaped cells with no convincing positive signal for cytokeratin (CK)18, PanCK and Wide CK (FIGS. 4A, C and E) and a strong positive signal for casein kinase 2β (FIG. 8).

The relevant isotype controls were also negative. Bars present 50 μm.

Figure 4:
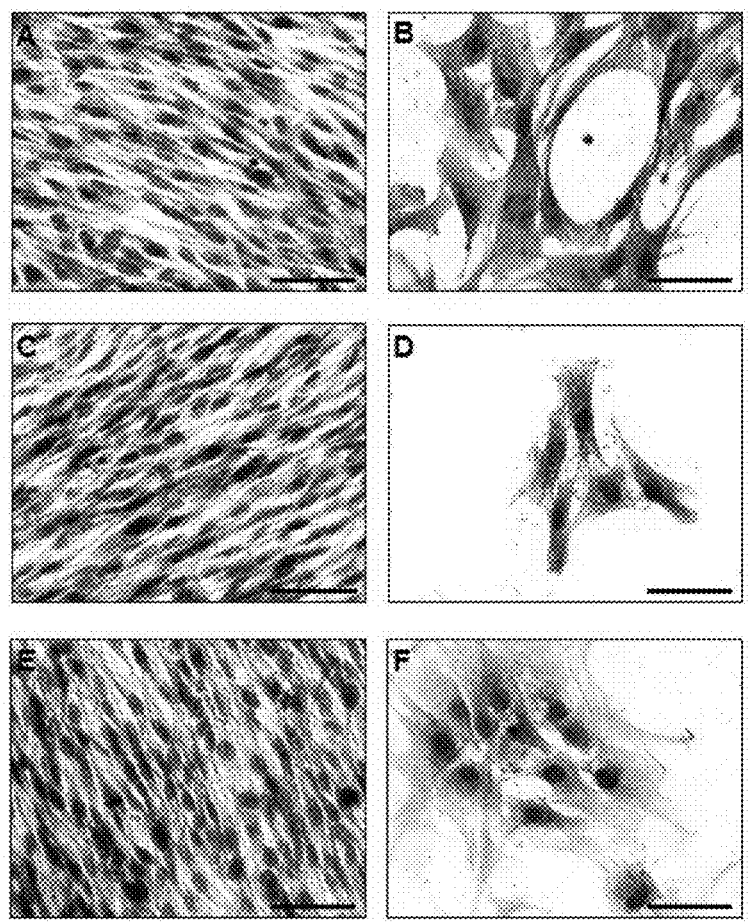
FIGS. 4, 5 and 6 show the results of a keratinocyte differentiation assay with EpSCs purified according to the current invention. EpSCs prior to differentiation were predominantly negative for specific keratinocyte markers (FIGS. 4A, C and E). After cultivation in specific keratinocyte differentiation inducing medium, the differentiated cells showed an altered morphology and were positive for keratinocyte markers (FIGS. 4B, D and F). The same switch in cytokeratin expression could be noticed in epidermospheres after 1 hour of adhesion (A) or on cytospins (B) (FIG. 5). Some of the differentiated cells were identified as myocytes (FIG. 6).
Figure 5:
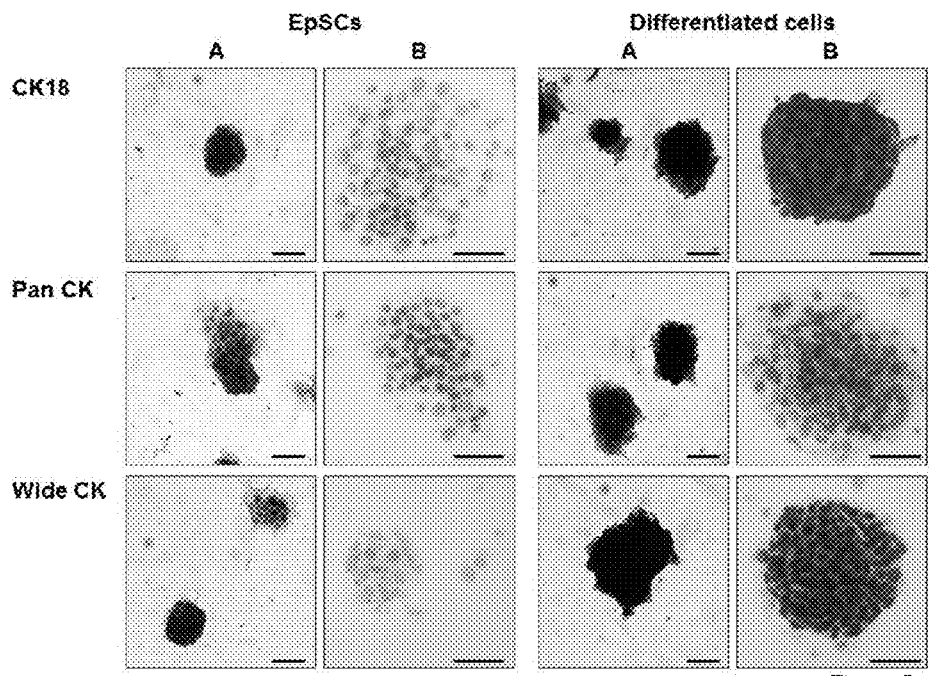
Figure 18:
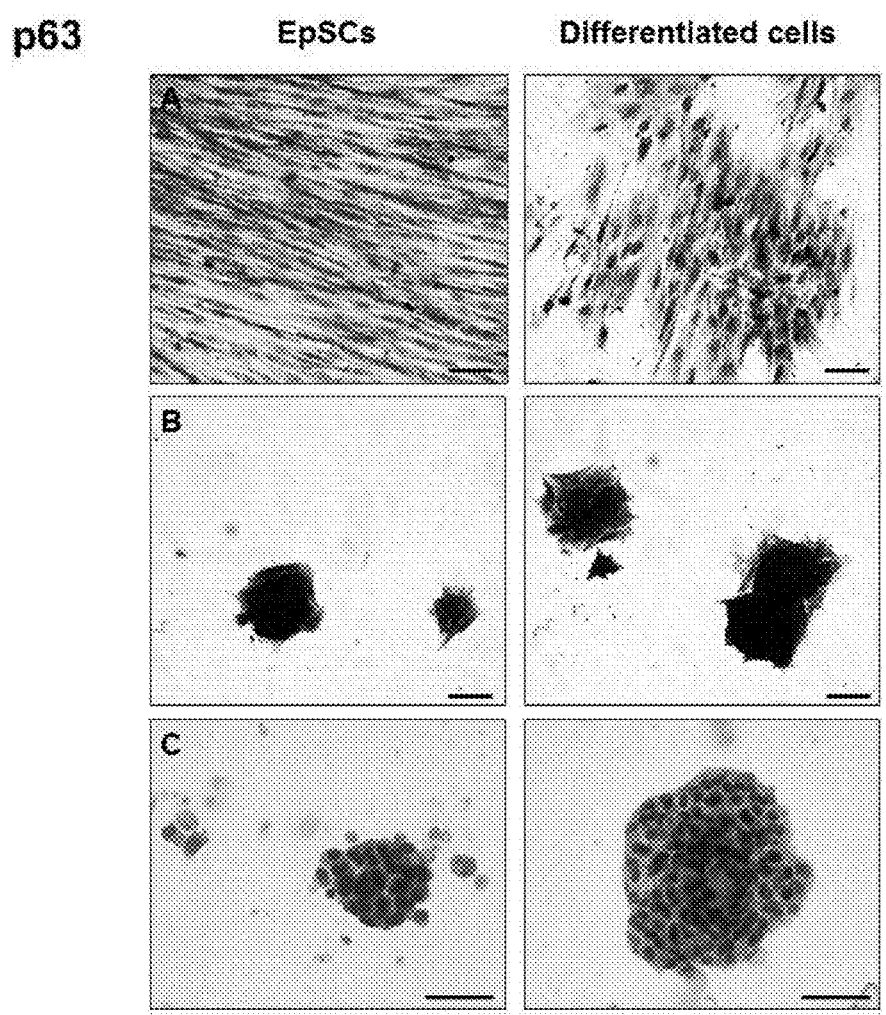
FIG. 18 shows expression of p63 in undifferentiated epithelial stem cells (EpSCs) and differentiated keratinocytes in adhesive cultures (A), epidermospheres after 1 hour of adherence (B) and epidermospheres on cytospins (C). Bars represent 50 µm.

After cultivation in the keratinocyte differentiation inducing medium, the cells became more stellate shaped with a strong positivity for the adult epithelial cell markers, CK18, PanCK and Wide CK (FIGS. 4B, D and F). In suspension, the same trend could be noticed (FIG. 5). After keratinocyte differentiation, expression of Ki67 and casein kinase 2β clearly decreased (FIG. 17). It has been previously reported that embryonic stem cells strongly upregulate CK18 expression during epithelial differentiation. In the present study EpSCs and differentiated cells expressed p63, which is an essential transcription factor for epithelial development, proliferation and differentiation (FIG. 18).

The relevant isotype control remained negative which indicated a specific binding of the aforementioned antibodies. Bars present 50 um.

In the keratinocyte differentiation medium some EpSCs became longitudinal stretched with the presence of smooth muscle actin (SMA) and vimentin (Vim), probably because of the addition of beta-mercaptoethanol. These markers confirmed that these cells were probably myocytes (FIG. 6). Bars present 50 um.

Differentiation towards adipocytes

Plant $5\times10^4$ cells/cm$^2$ in 4 wells of a 4-well culture plate.
A) EPITHELIAL CONTROL
    Culture for 3 days in EpSC medium in the 4- or 24-well plate.
B) ADIPOGENIC DIFFERENTIATION
    Culture for 3 days in adipogenic inducing medium in the 4- or 24-well plate.

Figure 7:
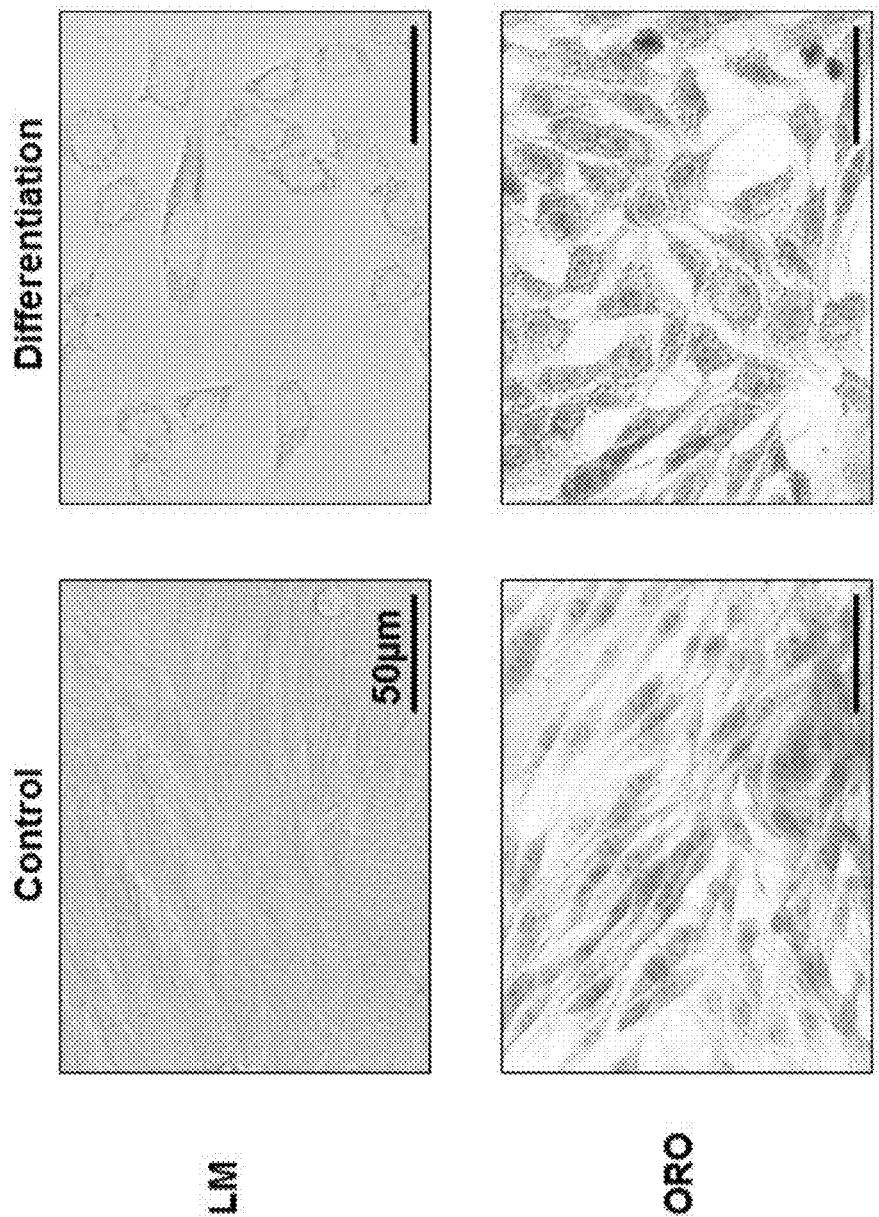
FIG. 7 shows the results of culturing the obtained EpSCs according to the current invention in an adipogenic differentiation inducing medium.

Cultivating in an adipogenic differentiation inducing medium, transformed the EpSCs in round cells with a lot of granules which could already be noticed light microscopically (LM). After performing an Oil Red O (ORO) staining, the presence of lipids was confirmed (FIG. 7). As a control, EpSCs were cultivated in their normal maintenance medium for the same period and with performing the same staining procedure as well (FIG. 7).

2d) Flow Cytometry

Plant at least $5\times10^4$ EpSC/T$_{75}$ flask in one flask.
    Trypsinize at 70-80% confluency and perform FLOW CYTOMETRY with the following MARKERS: Ki67, CD29, CD44, CD49f, CD90, MHC I, MHC II and CD105

The epidermosphere-derived cells were strongly positive (approximately 99±1%) for the following EpSC markers: CD29, CD44, CD49f and CD90. Since these markers can also be present on mesenchymal stem cells (MSCs), we tested with a marker specific for MSCs, CD105. This marker was negative on our EpSCs. The EpSCs were also negative for MHC II, low in MHC I (FIG. 19) and positive for the proliferation marker Ki67, which indicated the low immunogenicity of the isolated cells and the high division state the isolated cells were in. All markers were tested in parallel with relevant isotype controls in order to exclude aspecific binding of antibodies.

Example 2: Purification of EpSCs from a Horse Skin Sample from the Limbs

By using the method as outlined in the current invention, and the detailed protocol in example 1, EpSCs could be purified from an equine skin sample. Epithelial and dermal cell layer were separated prior to dissociation of the cells. A pure yield of EpSCS was obtained, as confirmed by the presence of epithelial stem cell markers Ki67, CD29, CD44, CD49f, CD90, p63 and/or CK2β. Cells were low in MHC I and negative for CD105, MHC II and CK18 markers which cross-reacted with equine mesenchymal stem cells. On the other hand, marker p63, typically absent on MSCs, was found to be present on EpSCs (FIG. 18). Hence, the latter proved again the specific epithelial nature of the isolated cells.

Example 3: Purification of EpSCs from Olfactory Epithelial Tissue of Adult Mice and Rats EpSCs can be purified from adult mouse and rat olfactory epithelium and vomeronasal organ using the methods described in Examples 1 and 2.

Adult mice and rats were anaesthetized with an overdose of somnitol, and then decapitated. The olfactory and vomeronasal organ epithelia were stripped from the conchae and nasal septum and incubated in EpSC medium prior to the rest of the purification procedure. The epithelia were enzymatically and mechanically dissociated as described in example 1. Cells were plated under ultralow-attachment conditions. Small clusters of epidermospheres were formed and seen floating in the medium. The cells purified from adult olfactory epithelia are self-renewing and multipotent, and thus are EpSCs.

Example 4: Purification of EpSCs from Mouse Tongue

EpSCs could equally be derived from tongue epithelia. The tongue was dissected to remove the epithelial layer that contains the sensory receptors and their underlying basal cells. This layer of tissue was dissociated to produce single cells and the single cells were plated in flasks containing EpSC medium, as described in example 1. After two to three days in a 37° C., 5% $CO_2$ tissue culture incubator, greater than 99% of the cells in the culture were dead or dying. Eventually, a pure composition of EpSCs was obtained. These EpSCs can be passaged using the same techniques as used for the multipotent stem cells derived from mammalian skin as in example 1.

Similarly, the EpSCs can be differentiated into keratinocytes or adipocytes using the techniques described herein.

Example 5: Purification of EpSCs from Mouse Skin

Skin from neonatal mice aged 3-15 days was isolated, the epidermal layer was removed from the dermal layer, dissociated and cultured in ultralow-attachment flasks with EpSC medium. A small population of cells proliferated and formed small cell clusters growing in suspension, the epidermospheres.

Subsequently, these larger clusters were isolated, dissociated and passaged. By this process of selective adhesion, substantially pure populations of floating clusters were obtained. These clusters eventually gave rise to a pure population of EpSCs as confirmed by some of the markers as discussed in example 1. Similar results were obtained by using skin from adult mice.

Example 6: Purification of EpSCs from Adult Human Skin

EpSCs were purified from the skin of a human forearm and from the human scalp or abdominal skin. Skin samples totalling 1 cm$^2$ or less from each of eight individuals were used. The skin included dermal and epidermal tissue. Prior to purification, the epidermal layer was separated from the dermal layer. EpSCs were purified specifically from the epidermal layer.

Figure 10:
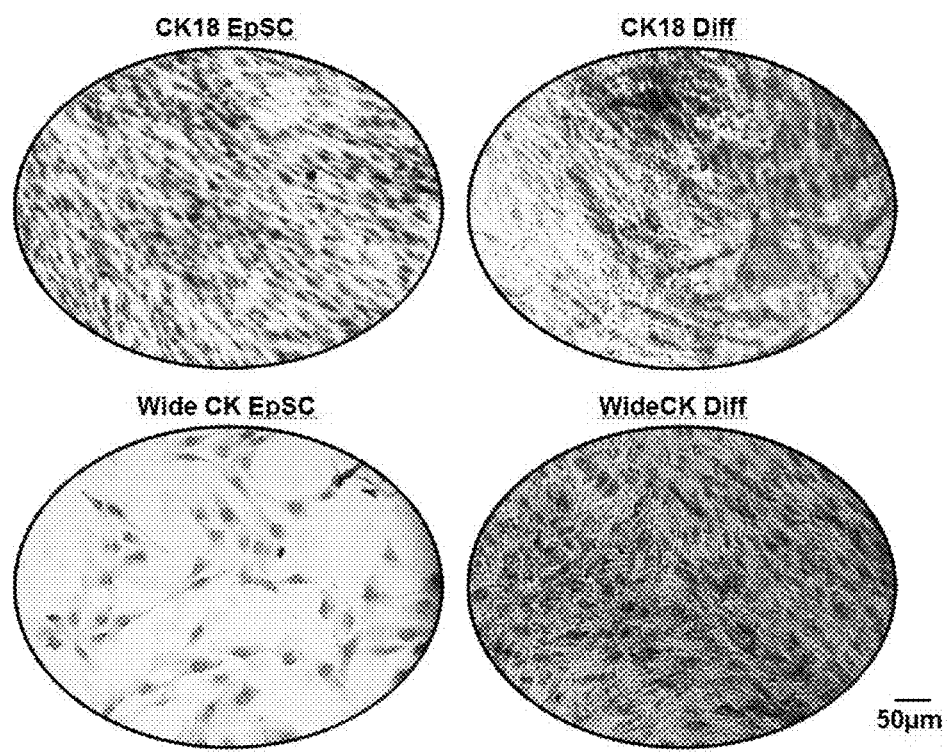
FIG. 10 depicts immunocytochemistry experiments of cytokeratin 18 (CK18) and Wide CK on both undifferentiated (negative) and differentiated (positive) human EpSCs purified according to an embodiment of the current invention.

Tissue was cut into smaller pieces and enzymatically dissociated according to example 1. Cells were plated under ultralow-attachment conditions and resulting epidermospheres were isolated. Presence of EpSCs in the resulting cellular suspension was confirmed by the appropriate markers as described in the current invention. Cells were able to differentiate, e.g. in keratinocytes and adipocytes, confirming the multipotent state of the purified EpSCs. FIGS. 10 to 12 depict marker detection of human derived EpSCs according to the current invention. Human EpSCs were shown to be positive for casein kinase 2β, vimentin and Ki67 (FIG. 11, FIG. 12 for vimentin only) and for p63 (data not shown). Purified EpSCs were shown negative for cytokeratin 18 (FIG. 12) and CD105, this in contrast to mesenchymal stem cells (FIG. 13). Mesenchymal stem cells were positive for both cytokeratin 18 and vimentin (FIG. 13).

Example 7: In Vivo Study a) Administration of EpSCs

After local anaesthesia and surgical preparation, 6 full-thickness skin wounds of approximately 4 cm$^2$ were induced in a 5-year-old gelded horse dorsally from the musculus gluteus medius (3 on the left side and 3 on the right side). Three randomly assigned wounds received allogenic putative EpSCs (derived from a horse skin sample according to Example 1) in combination with autologous platelet-rich-plasma PRP (EpSC/PRP-treatment) as a carrier, and the three remaining wounds were treated in exactly the same way, but without putative EpSCs (PRP injection only). The EpSC/PRP-treatment consisted of 2 approaches: first, an intradermal injection (0.5 ml in each of the 4 wound edges) of 1 ml of DMEM containing 8×106 freshly prepared putative EpSCs at passage 3 in combination with 1 ml of PRP (prepared as previously described (Beerts et al., 2013; Broeckx et al., 2012)) was performed. Immediately afterwards, a topical application of 0.5 ml DMEM containing 4×10$^6$ putative EpSCs and 0.5 ml of PRP was performed. The topical application was repeated after absorption of the liquid, which was after 24 hours. The PRP-treatment was performed in exactly the same manner; however, the DMEM did not contain EpSCs in this group. Wounds were not sutured, but covered with an adhesive, non-absorbable plastic in which micropores were made in order to allow oxygen access. The horse was bound in his stable for 24 hours in order to prevent rolling and pictures were taken every 3-4 days. Wounds were measured and surfaces were calculated right before the treatments and 30 days after the treatment by a double-blinded veterinarian. The experimental design was approved by the ethical committee.

b) Histology of Tissue Sections

On day 30, tissue samples were taken with a 8 mm punch biopsy in the centre of the wound (covering the whole wound area). Afterwards, the samples were fixed in neutral buffered 10% formalin, embedded in paraffin, sectioned at 4 µm thickness and stained with Hematoxylin & Eosin, Van Gieson and Elastin stains according to standard protocols.

All samples were blindly analyzed by an ECVP certified pathologist (SM) using a modified scoring system, adapted from Abramov (2007) and Babaeijandaghi (2010). Briefly, the epidermis was scored for thickness (0-3), crust formation (0-1), dermo-epidermal separation (0-2), and completeness of re-epithelization (0-3) (Table I). Sections of positive control skin are originating from the same horse, and were made from the samples removed at the moment of wound induction (and should obtain a maximal score). The dermis was evaluated using 6 main parameters: (i) edema (0-3); (ii) amount and morphology of the stroma (thickness measured and scored 0-3, amount of collagen and the morphology of collagen fibers (thin/immature, intermediate or thick/mature) using Van Gieson (VG) stain and scored 0-2, amount of elastin using elastica Van Gieson (eVG) stain and scored 0-1), (iii) thickness and morphology of the granulation tissue (thickness measured and scored 0-3, maturation of fibroblasts scored 0-3), (iv) neovascularization (scored 0-3 and average number of capillaries counted per 200× magnification field on immunohistochemical stain for von Willebrand factor (vWF), (v) acute inflammation/neutrophilic infiltrate (0-3), and (vi) chronic inflammation/lymphoplasmacytic infiltrate (0-3). Again, positive control samples would obtain a maximal score. The average of 3 fields was used to evaluate different histopathological parameters and all measurements were performed with a computer-based program (LAS V4.1, Leica Microsystems).

TABLE 1

Different skin healing parameters that were scored in the present study (adapted from Abramov and Babaeijandaghi)

| | PARAMETER | SCORE |
|---|---|---|
| EPIDERMIS | Acanthosis | 0 = severe (>15 layers) or moderate irregular, 1 = moderate regular (10-15 layers), 2 = mild (5-10 layers), 3 = none |
| | Crust | 0 = present, 1 = absent |

TABLE 1-continued

Different skin healing parameters that were scored in the
present study (adapted from Abramov and Babaeijandaghi)

| | PARAMETER | | SCORE |
|---|---|---|---|
| DERMIS | Dermo-epidermal separation | | 0 = multifocal to diffuse, 1 = focal, 2 = none |
| | Re-epithelization | | 0 = none, 1 = scant, 2 = complete but immature/thin, 3 = complete and mature |
| | Edema | | 0 = severe, 1 = moderate, 2 = mild, 3 = none |
| | Stroma | Collagen amount (VG stain) + thickness dermis | 0 = severely raised, 1 = moderately raised, 2 = mildly raised, 3 = normal |
| | | Collagen morphology (VG stain) | 0 = mostly amorphous, 1 = mostly thin wavy, 2 = mostly thick wavy |
| | | Elastin amount (eVG stain) | 0 = not/scarce in repair tissue, 1 = few in repair(ed) tissue, 2 = normal distribution and amount |
| | | Maturation fibroblasts | 0 = none, 1 = mild, 2 = moderate, 3 = full |
| Granulation tissue | Amount + thickness measured | | 0 = abundant, 1 = moderate, 2 = mild, 3 = none |
| Neovascularization | Number of capillaries per 200x field, (vWF IHC) | | 0 = abundant (25-35 per 200x), 1 = moderate (15-25 per 200x), 2 = mild (up to 15 vessels per 200x), 3 = none |
| Acute inflammation | | | 0 = abundant, 1 = moderate, 2 = mild, 3 = none |
| Chronic inflammation | | | 0 = abundant, 1 = moderate, 2 = mild, 3 = none |

VG = Van Gieson;
vWF = Von Willebrand Factor c) Immunohistochemistry on Tissue Sections In order to localize epithelial cells within the epidermis, skin glands and hair follicles, Pan CK and Wide CK were used. Casein Kinase 2β and Ki67 indicated where the proliferating epithelial cells were located. To examine the role of EpSCs in elastin production and neovascularization, tissue sections were stained with mouse anti-bovine elastin IgG1 (Leica, clone BA-4, 1:100) and rabbit anti-human vWF (Dako, 1:6400), respectively. Finally, vimentin and smooth muscle actin (SMA) were used to localize myofibroblasts. Immunolabeling was achieved with a high-sensitive horseradish peroxidase mouse or rabbit diaminobenzidine kit (Envision DAB+kit, Dako) in an autoimmunostainer (Cytomation S/N S38-7410-01, Dako). This kit also blocked endogenous peroxidase. A commercially available antibody diluent (Dako) with background-reducing components was used to block hydrophobic interactions. All skin samples (including positive and negative controls) were submitted to the same immunohistochemistry staining.

d) Statistical Analysis

Data were analyzed using the two-tailed Students t-test for group comparisons of normally distributed variables. Values are given as means±standard deviation (bars). P-values were calculated using an Excel spreadsheet (2007; Microsoft Corp., Redmond, Wash., USA), and P<0.05 was considered a probability of significant difference between compared groups of samples.

f) Results

Figure 14:
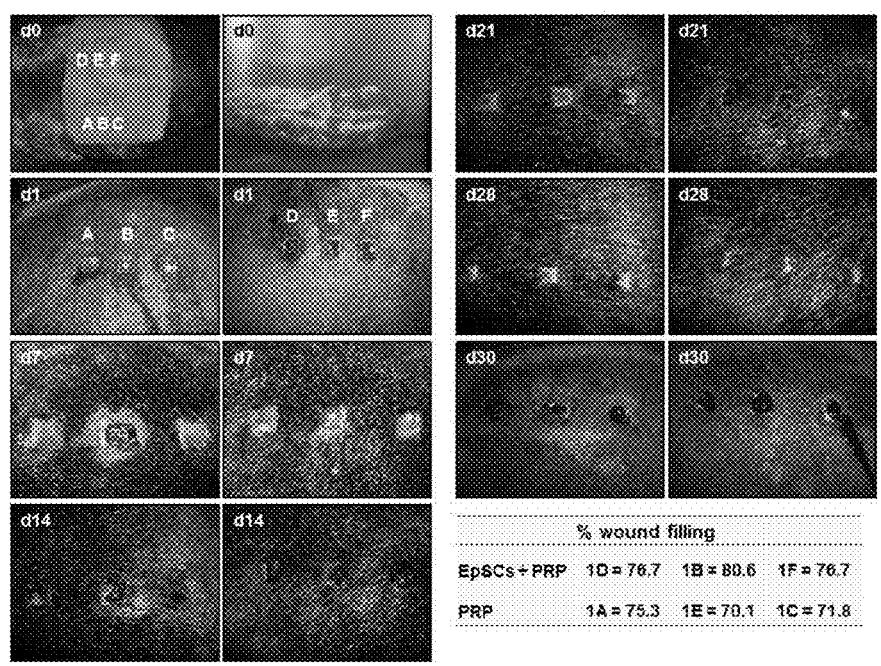
FIG. 14 shows the evaluation of macroscopic wounds treated with or without cellular compositions according to an embodiment of the current invention. Macroscopic images of the wound site at different time points (d=day) after platelet-rich plasma (PRP)-treatment with (B, D & F) and without (A, C & E) skin-derived epithelial stem cells (EpSCs). At each time point the left picture represents wounds A-C at the left side of the horse and the right picture wounds D-F at the right side. Table I represents the percentage of wound filling, calculated after measuring the areas before treatment (after wound induction at d0) and 30 days later (d30). In the EpSC/PRP-treated wounds, a significantly larger area was filled at d30.

Wounds were measured at the day of induction and again 30 days later (FIG. 14). Despite the performing veterinarian perceiving no difference, surface calculations were performed by dividing the remaining repair tissue in $mm^2$ by the initial wound area in $mm^2 \times 100$. This revealed an average of 79% (100%—surface calculation) of the wound surface that was filled (granulation and epithelialization) in the EpSC/PRP-treated group, which was significantly different (P=0.0083) from 72% for the PRP-treated group (FIG. 14).

Figure 15:
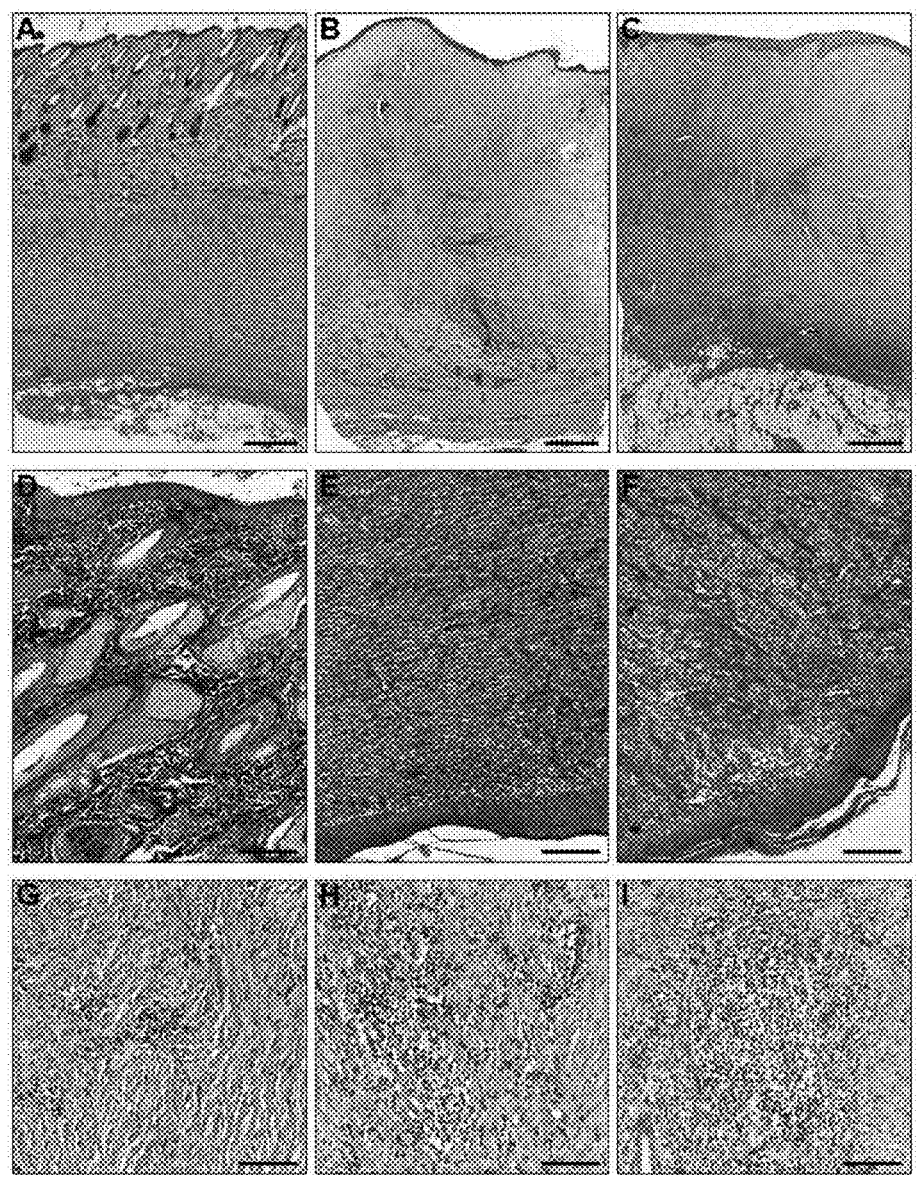
FIG. 15 shows Hematoxylin-Eosin (A-C & G-I) and Van Gieson (D-F) stainings on intact skin samples (A & D), PRP-treated group (B & E) and EpSC/PRP-treated (C & F) group. Chronic inflammation was evaluated by mild (G), moderate (H) or abundant (I) lymphocyte and plasma cell infiltration. Scale bars represent 1 mm (A-C), 200 µm (D-F) and 100 µm (G-I).

In all skin samples a normal to mild acanthotic, mature epidermis with crust formation (FIGS. 15B, C, E and F) was constituted at day 30. Image-based length measurements revealed a considerably higher amount of collagen and significantly (P=0.017) thicker dermis in the PRP-treated samples (7.4±0.6 mm, FIGS. 15B & E) compared to the EpSC/PRP-treated (5.6±0.9 mm, FIGS. 15C & F) and positive control samples (5.7±0.4 mm, FIGS. 15A & D). PRP-treated wounds also contained a considerably higher amount of granulation tissue (6.4±0.4 mm), compared to the EpSC/PRP-treated wounds (5.1±0.8 mm). In all skin samples, a mild acute inflammation (polymorphonuclear cells) was present and in 5 out of 6 cases a mild (FIG. 15G) to moderate (FIG. 15H) chronic inflammation (lymphocytes and plasma cells) was observed that was mainly restricted to perivascular, yet in some instances extended to interstitial regions. In one sample from the PRP-treated group an abundant number of inflammatory cells could be noticed in a localized area (FIG. 15I). There were no significant differences in histopathology scoring concerning the degree of edema and the morphology of the dermal stroma or granulation tissue.

Figure 16:
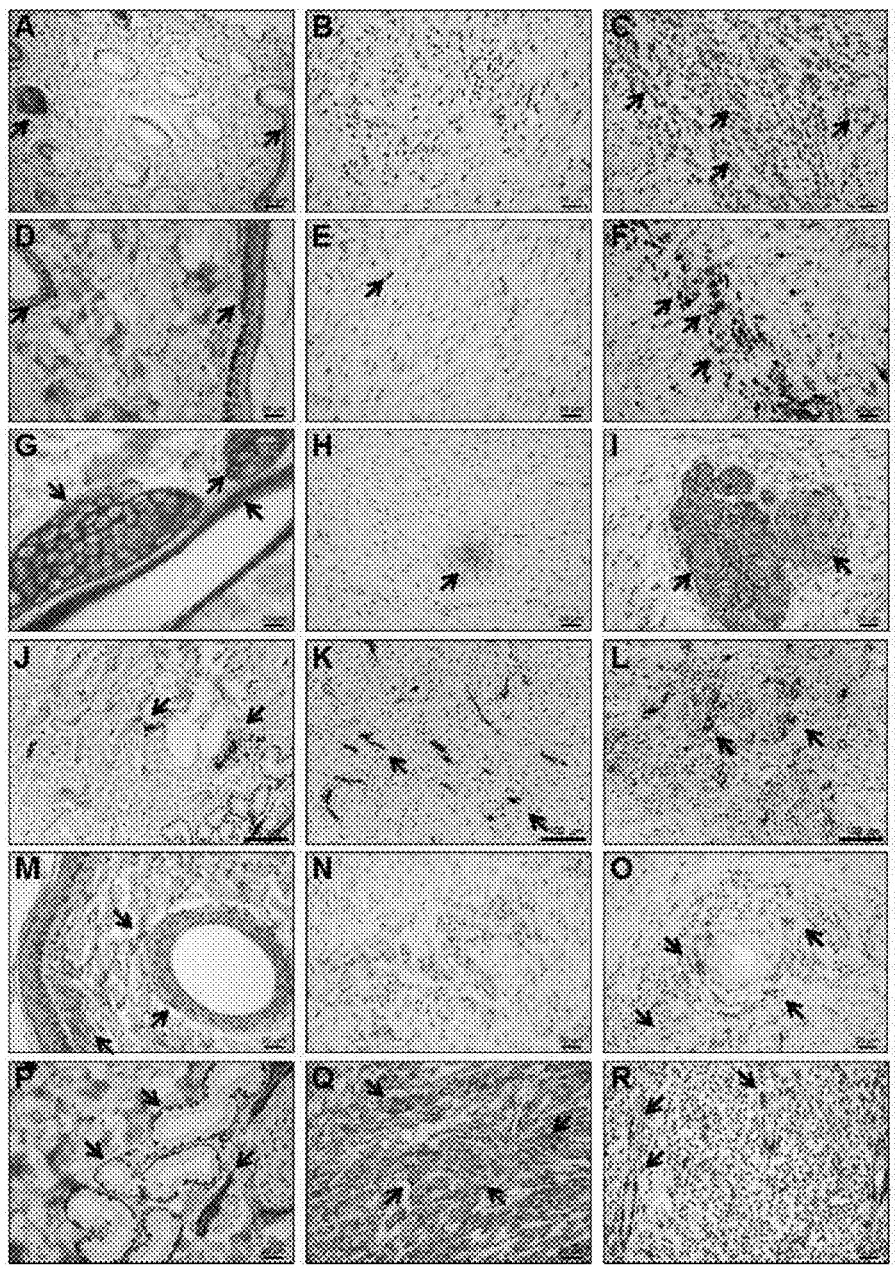
FIG. 16 depicts immunohistochemistry staining on the intact skin samples (left column: A, D, G, J, M, P), PRP-treated group (middle column: B, E, H, K, N, Q) and EpSC/PRP-treated group (right column: C, F, I, L, O, R). Casein Kinase 26 (A-C) and Ki67 (D-F) indicate the location of the EpSCs, whereas Pan cytokeratin (CK) and Wide CK (G-I) show the location of adult keratinocytes. Neovascularisation is visualized after staining with Von Willebrand Factor (J-L). Elastin (M-O) production and Smooth Muscle Actin (SMA)-positive myofibroblasts (P-R) were also evaluated. Besides the scale bars of "A, J, K & L" which are 100 µm, all bars represent 20 µm.

When evaluating Casein Kinase 2β and Ki67—which were positive on the EpSCs and decreased during differentiation—only some cells in the epidermal basal cell layer and the transition of the dermal papilla to bulge regions of the hair follicle stained positively (FIGS. 16A & D). Moreover, the EpSC/PRP-treated wounds revealed areas with many potential EpSCs that stained positively for Casein Kinase 2β (FIG. 16C) and Ki67 (FIG. 16F), whereas PRP-treated wounds contained at most a single positive cell per 400× magnification field (FIGS. 16B & E). When evaluating different keratinocyte markers (Wide CK and Pan CK) on the intact skin sections, epidermal cells and adnexal gland and hair follicle cells stained undoubtedly positive (FIG. 16G). When evaluating these markers on follicle-like structures, it became clear that these structures were more developed in the EpSC/PRP-treated group (FIG. 16I) than in the PRP-treated group (FIG. 16H). Neovascularisation was evaluated by means of Von Willebrand Factor staining and a considerably, but non-significantly (P=0.26), higher average of 31±4 blood vessels per 200× magnification field was noticed in the EpSC/PRP-treated wounds (FIG. 16L) compared to 23±4 vessels in the PRP-treated wounds (FIG. 16K).

Whereas general elastin staining revealed no considerable differences between the EpSC/PRP- and PRP-treated skin samples (data not shown), immunohistochemistry revealed a remarkable higher elastin production around follicle-like structures, strongly resembling intact skin structures (FIG. 16M) in the EpSC/PRP-treated group (FIG. 16O), compared to a scarce amount of elastin in the PRP-treated group (FIG. 16N). Smooth muscle actin (SMA) staining revealed a thin line of myogenic cells around the hair follicles and the blood vessels (FIG. 16P). Remarkably, the PRP-treated wounds contained dense areas of SMA positive cells in the dermis (FIG. 16Q), whereas the EpSC/PRP-treated wounds only revealed a thin lamina of myogenic cells around the follicle-like structures (FIG. 16R). Vimentin staining (data not shown) confirmed that these SMA positive areas in the PRP-treated group likely represented areas rich in myofibroblasts.

REFERENCES

Abramov Y, B Golden, M Sullivan, S M Botros, J J Miller, A Alshahrour, R P Goldberg and P K Sand, 2007. Histologic characterization of vaginal vs abdominal surgical wound healing in a rabbit model. Wound Repair Regen 15:80-6.

Babaeijandaghi F, I Shabani, E Seyedjafari, Z S Naraghi, M Vasei, V Haddadi-Asl, K K Hesari and M Soleimani, 2010. Accelerated epidermal regeneration and improved dermal reconstruction achieved by polyethersulfone nanofibers. Tissue engineering. Part A 16:3527-36.

Beerts C, C Seifert, M Zimmerman, E Felix, M Suls, T Marien, S Broeckx and J H Spaas. (2013). Desmitis of the accessory ligament of the equine deep digital flexor tendon: a regenerative approach. Journal of Tissue Science & Engineering. 4(1), 1-7.

Broeckx S, M Zimmerman, D Aerts, B Seys, M Suls, T Marien and J H Spaas. (2012). Tenogenesis of equine peripheral blood-derived mesenchymal stem cells: in vitro versus in vivo. Journal of Tissue Science & Engineering S11-001, 1-6.

Chen J S, Wong V W, Gurtner G C, 2012. Therapeutic potential of bone marrow-derived mesenchymal stem cells for cutaneous wound healing. Front Immunol. 2012, 3:192.

Dalal J, Gandy K, Domen J, 2012. Role of mesenchymal stem cell therapy in Crohn's disease. Pediatr. Res. 2012, 71 (4 Pt2): 445-51.

Deshiere A, Duchemin-Pelletier E, Spreux E, Ciais D, Combes F, Vandenbrouck Y, Couté Y, Mikaelian I, Giusiano S, Charpin C, Cochet C, Filhol O, 2012. Unbalanced expression of CK2 kinase subunits is sufficient to drive epithelial-to-mesenchymal transition by Snaill induction. Oncogene. May 7. doi: 10.1038/onc.2012.165.

Draheim K M, Lyle S, 2011. Epithelial stem cells. Methods Mol Biol 750, 261-274.

Fujimori Y, Izumi K, Feinberg S E, Marcelo C L, 2009. Isolation of small-sized human epidermal progenitor/stem cells by Gravity Assisted Cell Sorting (GACS). J Dermatol Sci 56, 181-187.

Gerseman M, Stange E F, Wehkamp J, 2011. From intestinal stem cells to inflammatory bowel diseases. World J. Gastroenterol. 2011, Jul. 21; 17(27):3198-203

Grandi F, Firmo B F, Colodel M M, Rocha R M, Werner J, Rocha N S, 2012. The importance of follicular stem cells in veterinary medicine in the context of skin tumours. Vet Dermatol 23, 81-82.

Lim M N, N H Hussin, A Othman, T Umapathy, P Baharuddin, R Jamal and Z Zakaria. (2012). Ex vivo expanded SSEA-4+ human limbal stromal cells are multipotent and do not express other embryonic stem cell markers. Mol Vis 18, 1289-300.

Nowak J A, Fuchs E, 2009. Isolation and culture of epithelial stem cells. Methods Mol Biol 482, 215-232.

Petersen O W, Ronnov-Jessen L, Howlett A R, Bissell M J, 1992. Interaction with basement membrane serves to rapidly distinguish growth and differentiation pattern of normal and malignant human breast epithelial cells. Proc Natl Acad Sci USA 89, 9064-9068.

Reinshagen H, C Auw-Haedrich, R V Sorg, D Boehringer, P Eberwein, J Schwartzkopff, R Sundmacher and T Reinhard. (2011). Corneal surface reconstruction using adult mesenchymal stem cells in experimental limbal stem cell deficiency in rabbits. Acta Ophthalmol 89, 741-8.

Roomans G M. 2010. Tissue engineering and the use of stem/progenitor cells for airway epithelium repair. Eur Cell mater. 2010 Jun. 23; 19:284-99.

Singer, A. J., Clark, R. A. (1999). Cutaneous wound healing. N Engl J Med 341, 738-746.

Spaas J H, Chiers K, Bussche L, Burvenich C, Van de Walle G R, 2012. Stem/progenitor cells in non-lactating versus lactating equine mammary gland. Stem Cells and Development 21, 3055-3067.

Sundberg, P. (2004). "Skin and adnexa of the laboratory mouse," in The Laboratory Mouse, edsH. Hedrich and G. Bullock (SanDiego, Calif.: Elsevier Academic Press), 195-206.

Staniszewska M, Sluczanowska-Glabowska S, Drukala J, 2011. Stem cells and skin regeneration. Folia Histochem Cytobiol 49, 375-380.

Stingl J, Eaves C J, Zandieh I, Emerman J T, 2001. Characterization of bipotent mammary epithelial progenitor cells in normal adult human breast tissue. Breast cancer research and treatment 67, 93-109.

Wilmink, J. M., Stolk, P. W., van Weeren, P. R., Barneveld, A. (1999a). Differences in second-intention wound healing between horses and ponies: macroscopic aspects. Equine Vet J 31, 53-60.

Wilmink, J. M., van Weeren, P. R., Stolk, P. W., Van Mil, F. N., Barneveld, A. (1999b). Differences in second-intention wound healing between horses and ponies: histological aspects. Equine Vet J 31, 61-67.

What is claimed is:

1. A method for obtaining a cellular composition comprising epithelial stem cells (EpSCs) derived from the epidermal layer, whereby said composition comprises at least 90% of viable EpSCs, comprising the steps of:
   obtaining a mammalian skin sample;
   at least partially separating the epidermal layer from the dermal layer;
   obtaining a cell suspension from said epidermal layer by performing at least one enzymatic dissociation step;
   culturing said cell suspension under low-attachment conditions;
   selecting non-adherent cells; and
   amplifying the selected cells under adherent conditions.

2. Method according to claim 1, further comprising the step of selecting cells in said cell suspension based on cell diameter, prior to said culturing of cell suspension.

3. Method according to claim 2, wherein said cell diameter of the selected cells is between 5 and 150 μm.

4. Method according to claim 1, wherein said cell suspension is cultured in cell medium comprising growth factors, selected from the group consisting of FGF, bFGF, EGF and combinations thereof.

5. Method according to claim 1, wherein said non-adherent cells comprise at least 90% epithelial stem cells.

6. Method according to claim 1, wherein said cellular composition comprises EpSCs which express p63 and at least one molecular marker selected from the group consisting of CD29, CD44, CD49f, CD90, Ki67, and Casein Kinase 2β and/or are negative for molecular marker CD105, and/or CK18.

7. Method according to claim 1, wherein said EpSCs are equine derived.

8. Method according to claim 2, wherein said non-adherent cells comprise at least 90% epithelial stem cells.

9. Method according to claim 3, wherein said non-adherent cells comprise at least 90% epithelial stem cells.

10. Method according to claim 4, wherein said non-adherent cells comprise at least 90% epithelial stem cells.

* * * * *